US005846714A

United States Patent [19]
Haskill et al.

[11] Patent Number: 5,846,714
[45] Date of Patent: Dec. 8, 1998

[54] METHOD OF IDENTIFYING A CHEMICAL THAT ALTERS DISSOCIATION OF AN NF-KB/IKB COMPLEX

[75] Inventors: John Stephen Haskill; Albert S. Baldwin, Jr., both of Chapel Hill, N.C.; Peter Ralph, Orinda, Calif.

[73] Assignees: Chiron Corporation, Everyville, Calif.; Unversity of North Carolina, Chapel Hill, N.C.

[21] Appl. No.: 475,359

[22] Filed: Jun. 7, 1995

Related U.S. Application Data

[62] Division of Ser. No. 119,891, Sep. 10, 1993, abandoned, which is a continuation of Ser. No. 702,770, May 17, 1991, abandoned.

[51] Int. Cl.⁶ ...................................................... C12Q 1/68
[52] U.S. Cl. ...................................................... 435/6
[58] Field of Search ......................... 435/6, 7.8; 436/501; 530/350; 536/23.5

[56] References Cited

U.S. PATENT DOCUMENTS

| | | | |
|---|---|---|---|
| 4,399,216 | 8/1983 | Axel et al. ................................... | 435/6 |
| 4,419,446 | 12/1983 | Howely et al. ........................ | 435/69.1 |
| 4,601,978 | 7/1986 | Karin ...................................... | 435/69.1 |
| 4,656,134 | 4/1987 | Ringold .................................. | 435/69.1 |
| 4,666,848 | 5/1987 | Gelfand et al. ..................... | 435/252.33 |
| 4,683,195 | 7/1987 | Mullis et al. .............................. | 435/6 |
| 4,683,202 | 7/1987 | Mullis .................................... | 435/91.2 |
| 4,711,845 | 12/1987 | Gelfand et al. ........................ | 435/69.1 |
| 4,800,159 | 1/1989 | Mullis et al. ........................... | 435/91.2 |
| 4,803,164 | 2/1989 | Hitzeman et al. ..................... | 435/69.3 |
| 4,990,337 | 2/1991 | Kurihara et al. ........................ | 424/427 |
| 5,183,736 | 2/1993 | Pfahl et al. ................................. | 435/6 |
| 5,376,530 | 12/1994 | De The et al. ............................ | 435/6 |
| 5,385,915 | 1/1995 | Buxbaum et al. ....................... | 514/313 |

FOREIGN PATENT DOCUMENTS

| | | |
|---|---|---|
| 0 196 864 | 10/1986 | European Pat. Off. . |
| 0 236 069 | 9/1987 | European Pat. Off. . |
| 0 258 017 | 3/1988 | European Pat. Off. . |
| WO85/04899 | 11/1985 | WIPO . |
| WO89/08147 | 9/1989 | WIPO . |

OTHER PUBLICATIONS

Soukhanov et al (eds), Webster's II New Riverside University Dictionary, 1994, The Riverside Publishing Company, Houghton Mifflin Company, Boston, MA, p. 738.

Mitchell et al, Science, vol. 245: pp. 371–378 (Jul. 28, 1989).

Anderson, W.F., "Prospects for Human Gene Therapy", Science, 226:401–409 (1984).

Aviv et al., "Purification of Biologically Active Globin Messenger RNA by Chromatography on Oligothymidylic acis–Cellulose", Proc. Natl. Acad. Sci. (USA), 69:1408–1412 (1972).

Baeuerle et al., "Activation of DNA–Binding Activity in an Apparently Cytoplasmic Precursor of the NF–κB Transcription Factor", Cell, 53:211–217 (1988).

Baeuerle et al., "IκB: A Specific Inhibitor of the NF–κB Transcription Factor", Science, 242:540–546 (1988).

Baeuerle et al., "Activation of NF–κB: A Transcription Factor Controlling Expression of the Immunoglobulin κ Light–chain Gene and of HIV", in The Control of Human Retrovirus Gene Expression, pp. 217–226, Franz et al. eds., Cold Spring Harbor Laboratory Press, Cold Spring Harbor, NY (1988).

Baeuerle et al., "A 65–kD subunit of active NF–κB is required for inhibition of NF–κB by IκB", Genes and Development, 3:1689–1698 (1989).

Baldwin, A.S., "Analysis of Sequence–Specific DNA–Binding Proteins by the Gel Mobility Shift Assay", DNA & Protein Engineering Techniques, 2:73–76 (1990).

Baldwin et al., "Two transcription factors, NF–κB and H2TF1, interact with a single regulatory sequence in the class I major histocompatibilty complex promoter", Proc. Natl. Acad. Sci. (USA), 85;723–727 (1988).

Baldwin et al., "Binding of a Nuclear Factor to a Regulatory Sequence in the Promoter of the Mouse H–2K$^b$ Class I Major Histocompatibility Gene",Mol. Cell. Biol.7:305–313 (1987).

Balkwill et al., "The cytokine network", Immunol. Today, 10:299–303 (1989).

Bolivar et al., "Construction and Characterization of New Cloning Vehicles: II. A Multipurpose Cloning System", Gene, 2:95–113 (1977).

Böyum, A., "Isolation of Mononuclear Cells and Granulocytes from Human Blood",Scandinavian J. of Clinical Lab. Invest., 21:77–89 (1968).

Brini et al., "Cyclosporin A inhibits induction of IL–2 receptor α chain expression by affecting activation of NF–κB–like factor(s) in cultured human T lymphocytes", Eur. Cytokine Net., 1:131–139 (1990).

Broach et al., "Transformation in Yeast: Development of a Hybrid Cloning Vector and Isolation of the CAN1 Gene", Gene, 8:121–133 (1979).

Broach, J.R., "Construction of High Copy Yeast Vectors Using 2–μm Circle Sequences", Meth. Enzymol., 101:307–325 (1983).

Caput et al., "Identification of a common nucleotide sequence in the 3'–untranslated region of mRNA molecules specifying inflammatory mediators", Proc. Natl. Acad. Sci. (USA), 83:1670–1674 (1986).

Carthew et al., "An RNA Polymerase II Transcription Factor Binds to an Upstream Element in the Adenovirus Major Late Promoter", Cell, 43:439–448 (1985).

Chirgwin et al., "Isolation of Biologically Active Ribonucleic Acid from Sources Enriched in Ribonuclease", Biochemistry, 18:5294–5299 (1979).

(List continued on next page.)

Primary Examiner—Jerry A. Mckelvey
Attorney, Agent, or Firm—Marshall O'Toole; Jane E. R. Potter; Robert P. Blackburn

[57] ABSTRACT

Compositions and methods of using the same are described that have applications for the identification of prophylactics or therapeutics for the treatment of diseases resulting from altered gene expression, including genes that encode cytokines or related molecules.

6 Claims, 6 Drawing Sheets

OTHER PUBLICATIONS

Clarke et al., "Selection Procedure for Isolation of Centromere DNAs from *Saccharomyces cerevisiae*", *Meth. Enzymol.*, 101:300–307 (1983).

Clewell et al., "Supercoiled Circular DNA–Protein Complex in *Escherichia coli*: Purification and Induced Conversion to an Open Circular DNA Form", *Proc. Natl. Acad. Sci. (USA)*, 62:1159–1166 (1969).

Clewell, D.B., "Nature of Col $E_1$ Plasmid Replication in *Escherichia coli* in the Presence of Cholramphenicol", *J. Bacteriol.*, 110–667–676 (1972).

Cohen et al., "Nonchromosomal Antibiotic Resistance in Bacteria: Genetic Transformation of *Escherichia coli* by R–Factor DNA", *Proc. Natl. Acad. Sci. (USA)*, 69:2110–2114 (1972).

Depicker et al., "Nopaline Synthase: Transcript Mapping and DNA Sequence", *J. Mol. Appl. Genet.*, 1:561–573 (1982).

Eierman et al., "Human Monocyte Inflammatory Mediator Gene Expression is Selectively Regulated by Adherence Substrates", *J. Immunol.*, 142:1970–1976 (1989).

Fiers et al., "Complete nucleotide sequence of SV40 DNA", *Nature*, 273:113–120 (1978).

Folks et al., "Tumor necrosis factor α induces expression of human immunodeficiency virus in a Chronically infected T–cell clone", *Proc. Natl. Acad. Sci. (USA)*, 86:2365–2368 (1989).

Ghosh et al., "Activation in vitro of NF–κB by phosphorylation of its inhibitor IκB", *Nature*, 344:678–682 (1990).

Goeddel et al., "Synthesis of human fibroblast interferon by *E. coli*", *Nucl. Acids Res.*, 8:4057–4074 (1980).

Graham et al., "A New Technique for the Assay of Infectivity of Human Adenovirus 5 DNA", *Virology*, 52:456–467 (1973).

Greene, A. E., "Human Biopsy Material from Genetic Abnormalities", in *Tissue Culture: Methods and Application*, pp. 69–72, Kruse et al., eds., Academic Press, New York, NY (1973).

Hack et al., "Increased Plasma Levels of Interleukin–6 in Sepsis", *Blood*, 74:1704–1710 (1989).

Hanahan, D., "Studies on Transformation of *Escherichia coli* with Plasmids"*J. Mol. Biol.*, 166:557–580 (1993).

Haskill et al., "Adherence Iduces Selective mRNA Expression of Monocyte Mediators and Proto–Oncogenes", *J. Immunol.*, 140:1690–1694 (1988).

Hitzeman et al., "Isolation and Characterization of the Yeast 3–Phosphpglycerokinase Gene (PGK) by an Immunological Screening Technique", *J. Biol. Chem.*, 255:12073–12080 (1980).

Holland et al., "Isolation and Identication of Yeast Messenger Ribonucleic Acids Coding for Enolase, Glyceraldehyde–3–phosphate Dehydrogenase, and Phosphoglycerate Kinase", *Biochemistry*, 17:4900–4907 (1978).

Holland et al., "The Primary Structures of Two Yeast Enolase Genes: Homology Between The 5' Noncoding Flanking Regions Of Yeast Enolase And Glyceraldehyde Dehydrogenase Genes",*J. Biol. Chem.*, 256:1385–1395 (1981).

Hsiao et al., "High–frequency transformation of yeast by plasmids containing the cloned yeast ARG4 gene", *Proc. Natl. Acad Sci. (USA)*, 76:3829–3833 (1979).

Huynh et al., "Constructing and Screening cDNA Libraries in λgt10 and λgt11", in *DNA Cloning: A Practical Approach*, vol. 1, pp. 49–78, Glover ed., IRL Press, Oxford, UK (1985).

Ish–Horowicz et al., "Rapid and efficient cosmid cloning", *Nucl. acids Res.*, 9:2989–2998 (1981).

Kadonaga et al., "Affinity purification of sequence–specific DNA binding proteins", *Proc. Natl. Acad. Sci. (USA)*, 83:5889–5893 (1986).

Kaighn, M.E., "Human Liver Cells", in *Tissue Culture: Methods and Applications* pp. 54–58, Kruse et al. eds., Academic Press, New York, NY (1973).

Kasten, F.H., "Mammalian Myocardial Cells", in *Tissue Culture: Methods and Applications* pp. 72–81, Kruse et al. eds., Academic Press, New York, NY (1973).

Kawasaki et al., "Detection of Gene Expression", in *PCR Technology: Principles and Applications for DNA Amplification* pp. 89–97, Erlich ed., Stockton, NY (1989).

Kieran et al., "The DNA Binding Subunits of NF–κB Is Identical to Factor KBF1 and Homologous to the rel Oncogene Product", *Cell*, 62:1007–1018 (1990).

Laemmli, U.K., "Cleavage of Structural Proteins during the Assembly of the Head of Bacteriophage T4", *Nature*, 227;680–685 (1970).

Lenardo et al., "NF–$_k$B: A Pleiotropic Mediator of Inducible and Tissue–Specific Gene Control", *Cell*, 58:227–229 (1989).

Lux et al., "Analysis of cDNA for human erythrocyte ankyrin indicates a repeated structure with homology to tissue–differentiatation and cell–cycle control proteins", *Nature*, 344:36–42 (1990).

Maniatis et al., "In Situ Hybridization of Bacterial Colonies or Bacteriophage Plaques",in *Molecular Cloning: A Laboratory Manual*, pp. 312–328, Cold Spring Harbor Laboratory Press, Cold Spring Harbor, NY (1982).

Matteucci et al., "Synthesis of Deoxyoligonucleotides on a Polmer Support",*J. Am. chem. Soc.*, 103:3185–3191 (1981).

Maxam et al., "Sequencing End–Labeled DNA with Base–Specific Chemical Cleavages", *Meth. Enzymol.*, 65:499–560 (1980).

Messing et al., "A system for shotgun DNA sequencing", *Nucl. Acids Res.*, 9:309–321 (1981).

Miki et al., "Interleukin–6 (IL–6) functions as an in vito autocrine growth factor in renal cell carcinomas", *FEBS Letters*, 250:607–610 (1989).

Nabel et al., "An inducible transcription factor activates expression of human immunodeficiency virus in T cells", *Nature*, 326:711–713 (1987).

Okayama et al., "A cDNA Cloning Vector That Permits Expression of cDNA Inserts in Mammalian Cells", *Mol. Cell. Biol.*, 3:280–289 (1983).

Sanger et al., "DNA Sequencing with chain–terminating inhibitors", *Proc. Natl. Acad. Sci. (USA)*, 74:5463–5467 (1977).

Sen et al., "Multiple Nuclear Factors Interact with the Immunoglobulin Enhancer Sequences", *Cell*, 46:705–716 (1986).

Shaw et al., "A general method for the transfer of cloned genes to plant cells", *Gene*, 23:315–330 (1983).

Shimatake et al., "Purified λ regulatory protein cII positively activates promoters for lysogenic development", *Nature*, 292:128–132 (1981).

Singh et al., "A nuclear factor that binds to a conserved sequence motif in transcriptional control elements of immunglobulin genes", *Nature*, 319:154–158 (1986).

Sompayrac et al., "Efficient infection of monkey cells with DNA of simian virus 40", *Proc. Natl. Acad. Sci. (USA)*, 78:7575–7578 (1981).

Sporn et al., "Monocyte Adherence Results in Selective Induction of Novel Genes Sharing Homology with Mediators of Inflammation and Tissue Repair", *J. Immunol.*, 144:4434–4441 (1990).

Stinchcomb et al., "Isolation and characterisation of a yeast chromosomal replicator", *Nature*, 282:39–43 (1979).

Swick et al., "Functional analysis of GC element binding and transcription in the hamster dihydrofolate reductase gene promoter", *Nucl. Acids Res.*, 17:9291–9304 (1989).

Thorens et al., "Phagocytosis and Inflammatory Stimuli Induce GM–CSF mRNA in Macrophages through Posttranscriptional Regulation", *Cell*, 48:671–679 (1987).

Tschumper et al., "Sequence of a yeast DNA fragment containing a chromosomal replicator and the TRP1 gene", *Gene*, 10:157–166 (1980).

Uhlmann et al., "Antisense Olgonucleotides: A New Therapeutic Principle", *Chemical Reviews*, 90:543–584 (1990).

Ulmer et al., "Discontinuous Density Gradient Separation of Human Mononuclear Leucocytes Using Percoll® as Gradient Medium", *J. Immunol. Meth.*, 30:1–10 (1979).

Van Solingen et al., "Fusion of Yeast Spheroplasts", *J. Bacteriol.*, 130:946–947 (1977).

Wang et al., "Molecular Cloning of the Complementary DNA for Human Tumor Necrosis Factor", *Science*, 228:149–154 (1985).

Watson et al., "An Alternative Procedure for the Synthesis of Double–stranded cDNA for Cloning in Phage and Plasmid Vectors", in *DNA Cloning: A Practical Approach*, vol. 1, pp. 79–88, Glover ed., IRL Press, Oxford, UK (1985).

Zabel et al., "Purified Human IκB Can Rapidly Dissociate the Complex of the NF–κB Transcription Factor with Its Congnate DNA", *Cell*, 61:255–265 (1990).

```
  1 ctgacctggT GTCACTCCTG TTGAAGTGTG GGGCTGATGT CAACAGAGTT
 51 ACCTACCAGG GCTATTCTCC CTACCAGCTC ACCTGGGGCC GCCCAAGCAC
101 CCGGATACAG CAGCAGCTGG GCCAGCTGAC ACTAGAAAAC CTTCAGATGC
151 TGCCAGAGAG TGAGGATGAG GAGAGCTATG ACACAGAGTC AGAGTTCACG
201 GAGTTCACAG AGGACGAGCT GCCCTATGAT GATGACTGTG TGTTTGGAGG
251 CCAGCGTCTG ACGTTATGAG CAAAGGGGCT GAAAGAACAT GGACTTGCAT
301 ATTTGTACAA AAAAAAAAGT TTTATTTTTC TAAAAAAAAA AAAAAAAAAA
```

FIG. 1

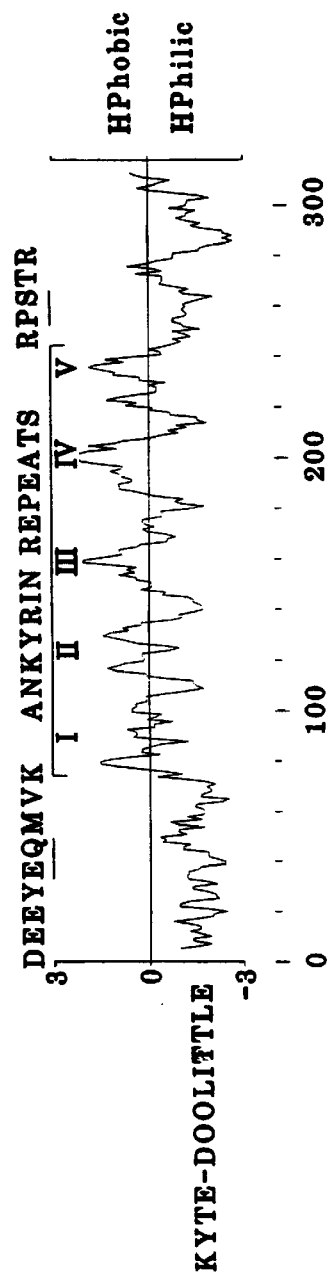

FIG. 3

```
TGCCGCCGTCCCGCCCGCCAGCGCCCCAGCGAGGAAGCAGCGCGCAGCCCGCGGCCCAGC      60
GCACCCGCAGCAGCGCCCGCAGCTCGTCCGCGCCATGTTCCAGGCGGCCGAGCGCCCCCA     120
                                  M  F  Q  A  A  E  R  P  Q       9
GGAGTGGGCCATGGAGGGCCCCCGCGACGGGCTGAAGAAGGAGCGGCTACTGGACGACCG     180
 E  W  A  M  E  G  P  R  D  G  L  K  K  E  R  L  L  D  D  R      29
CCACGACAGCGGCCTGGACTCCATGAAAGACGAGGAGTACGAGCAGATGGTCAAGGAGCT     240
 H  D  S  G  L  D  S  M  K  D  E  E  Y  E  Q  M  V  K  E  L      49
GCAGGAGATCCGCCTCGAGCCGCAGGAGGTGCCGCGCGGCTCGGAGCCCTGGAAGCAGCA     300
 Q  E  I  R  L  E  P  Q  E  V  P  R  G  S  E  P  W  K  Q  Q      69
GCTCACCGAGGACGGGGACTCGTTCCTGCACTTGGCCATCATCCATGAAGAAAAGGCACT     360
                      ankyrin I
 L  T  E  D  G  D  S  F  L  H  L  A  I  I  H  E  E  K  A  L      89
GACCATGGAAGTGATCCGCCAGGTGAAGGGAGACCTGGCCTTCCTCAACTTCCAGAACAA     420

T  M  E  V  I  R  Q  V  K  G  D  L  A  F  L  N  F  Q  N  N     109
CCTGCAGCAGACTCCACTCCACTTGGCTGTGATCACCAACCAGCCAGAAATTGCTGAGGC     480
                      ankyrin II
 L  Q  Q  T  P  L  H  L  A  V  I  T  N  Q  P  E  I  A  E  A     129
ACTTCTGGGAGCTGGCTGTGATCCTGAGCTCCGAGACTTTCGAGGAAATACCCCCCTACA     540

L  L  G  A  G  C  D  P  E  L  R  D  F  R  G  N  T  P  L  H     149
CCTTGCCTGTGAGCAGGGCTGCCTGGCCAGCGTGGGAGTCCTGACTCAGTCCTGCACCAC     600
                      ankyrin III
 L  A  C  E  Q  G  C  L  A  S  V  G  V  L  T  Q  S  C  T  T     169
CCCGCACCTCCACTCCATCCTGAAGGCTACCAACTACAATGGCCACACGTGTCTACACTT     660

P  H  L  H  S  I  L  K  A  T  N  Y  N  G  H  T  C  L  H  L     189
AGCCTCTATCCATGGCTACCTGGGCATCGTGGAGCTTTTGGTGTCCTTGGGTGCTGATGT     720
                      ankyrin IV
 A  S  I  H  G  Y  L  G  I  V  E  L  L  V  S  L  G  A  D  V     209
CAATGCTCAGGAGCCCTGTAATGGCCGGACTGCCCTTCACCTCGCAGTGGACCTGCAAAA     780
                      ankyrin V
 N  A  Q  E  P  C  N  G  R  T  A  L  H  L  A  V  D  L  Q  N     229
TCCTGACCTGGTGTCACTCCTGTTGAAGTGTGGGGCTGATGTCAACAGAGTTACCTACCA     840

P  D  L  V  S  L  L  L  K  C  G  A  D  V  N  R  V  T  Y  Q     249
GGGCTATTCTCCCTACCAGCTCACCTGGGGCCGCCCAAGCACCCGGATACAGCAGCAGCT     900
 G  Y  S  P  Y  Q  L  T  W  G  R  P  S  T  R  I  Q  Q  Q  L     269
GGGCCAGCTGACACTAGAAAACCTTCAGATGCTGCCAGAGAGTGAGGATGAGGAGAGCTA     960
 G  Q  L  T  L  E  N  L  Q  M  L  P  E  S  E  D  E  E  S  Y     289
TGACACAGAGTCAGAGTTCACGGAGTTCACAGAGGACGAGCTGCCCTATGATGACTGTGT    1020
 D  T  E  S  E  F  T  E  F  T  E  D  E  L  P  Y  D  D  C  V     309
GTTTGGAGGCCAGCGTCTGACGTTATGAGTGCAAAGGGGCTGAAAGAACATGGACTTGTA    1080
 F  G  G  Q  R  L  T  L                                          317
TATTTGTACAAAAAAAAAGTTTTATTTTTCTAAAAAAAGAAAAAAGAAGAAAAAATTTAA    1140
AGGGTGTACTTATATCCACACTGCACACTGCCTAGCCCAAAACGTCTTATTGTGGTAGGA    1200
TCAGCCCTCATTTTGTTGCTTTTGTGAACTTTTTGTAGGGGACGAGAAAGATCATTGAAA    1260
TTCTGAGAAAACTTCTTTTAAACCTCACCTTTGTGGGGTTTTTGGAGAAGGTTATCAAAA    1320
ATTTCATGGAAGGACCACATTTTATATTTATTGTGCTTCGAGTGACTGACCCCAGTGGTA    1380
TCCTGTGACATGTAACAGCCAGGAGTGTTAAGCGTTCAGTGATGTGGGGTGAAAAGTTAC    1440
TACCTGTCAAGGTTTGTGTTACCCTCCTGTAAATGGTGTACATAATGTATTGTTGGTAAT    1500
TATTTTGGTACTTTTATGATGTATATTTATTAAAGAGATTTTTACAAATG             1550
```

FIG. 2

FIG. 4A
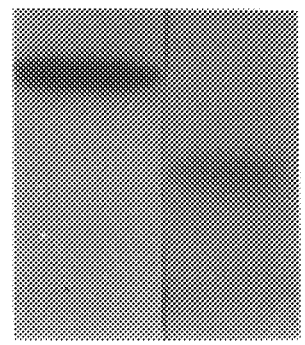
PROBE: MHC
EXTRACT: JURKAT +
RETIC: - WT Δ MT MT
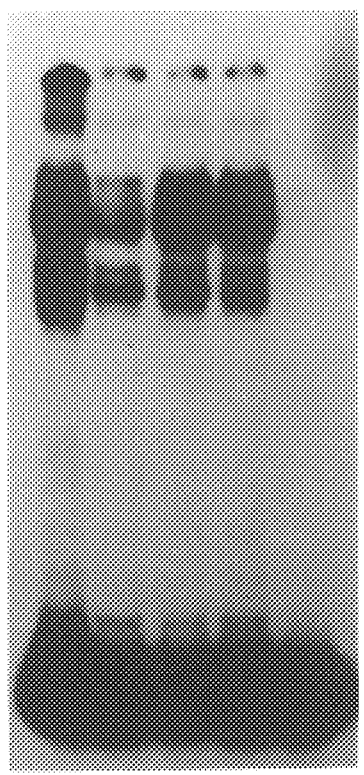
FIG. 4B
1 2 3 4 5

METHOD OF IDENTIFYING A CHEMICAL THAT ALTERS DISSOCIATION OF AN NF-KB/IKB COMPLEX

The present application is a division of U.S. patent application Ser. No. 08/119,891, filed Sep. 10, 1993, now abandoned, which is a continuation of U.S. patent application Ser. No. 07/702,770, filed May 17, 1991, now abandoned.

FIELD OF THE INVENTION

This invention is in the field of molecular biology/biochemistry. Described herein are compositions that have applications for the identification of prophylactics or therapeutics preferably for the treatment of viral diseases or diseases resulting from the undesirable production of cytokines or antibody. More specifically, an inhibitory material is shown that effects the transcriptional activity of genes that encode various proteins, including genes that encode cytokines or related molecules, viral proteins and immunoglobulin.

BACKGROUND OF THE INVENTION

Cytokines are small molecular weight proteins that have a myriad of biological functions (for background information, see Balkwill, F. R., et al., 1989, *Immun. Today*, 10:299). For example, cytokines are known to be capable of stimulating their own synthesis, as well as the production of other cytokines from a variety of cell types. They are also associated with disease. A good example is the presence of the cytokines interleukin-1 (IL-1) and tumor necrosis factor (TNF). IL-1 has been demonstrated to have multiple biological activities with the two prominent being fever production and lymphocyte activation. Moreover, both cytokines, alone or in combination, cause a shock state in animals that hemodynamically and hematologically is characteristic of septic shock in man caused by bacterial infection. TNF, in addition, has recently been shown to be involved in initiating the expression of human immunodeficiency virus in human cells that carry latent virus. Folks et al., 1989, *PNAS (USA)*, 86:2365. TNF and IL-1 also play a role in various autoimmune diseases, particularly arthritis. Duff, et al., 1987, *International Conference on Tumor Necrosis Factor and Related Cytotoxins*, 175:10.

In addition to IL, 1 and TNF, another cytokine, IL6, has recently been shown to be involved in infection, particularly sepsis, as well as in affecting the growth of tumor cells. Hack, et al. 1989, *Blood*, 74:1704, and Miki et al, 1989, *FEB*, 250: 607. IL,6 is also termed hybridoma growth factor, interferon-beta-2, B-cell stimulatory factor 2, 26 kD protein, and hepatocyte stimulating factor.

Adherence to an appropriate substratum has been shown to be important in transcriptional expression of cytokine mediators of inflammation produced by macrophages or monocytes, and adherence to different matrices has recently been shown to result in preferential gene induction (Sporn, S. A., et al., 1990, *J. of Immun.*, 144:4434 4441; Thorens, B., et al., 1987, *Cell*, 48:671). For example, within 30 minutes of monocyte adherence to plastic, a complex set of regulatory events is initiated as defined by rapid changes of mRNA levels of several inflammatory mediators and proto-oncogenes (Haskill, S., et al., 1988, *J.of Immunol.*, 140:1690). IL-1$\beta$, TNF-$\alpha$ and c-fos are rapidly elevated, whereas CSF-1 steady state mRNA levels increase by 90 minutes. In contrast, expression of c-fms and lysozyme is rapidly down-regulated. These genes are modulated by adherence to different biologically relevant substrates (Eierman, D. F., 1989, *J. of Immunol.*, 142:1970–1970).

Although high steady state mRNA levels of important mediators of inflammation are rapidly induced by adherence, adherence by itself is insufficient to cause efficient translation and secretion of IL-1$\beta$, TNF-$\alpha$, or CSF-1 (Haskill, S., et al., supra). Activation by a second signal, such as bacterial endotoxin, is required for the secretion of all three gene products. Thus, it is clear that signals derived from the act of adherence are likely to play a significant role in the activation and differentiation of monocytes allowing them to respond to infection and to influence the local tissue environment (Sporn, S. A, supra).

Recently, a protein termed NF-$\kappa$B has been shown to be a transcriptional activator (Sen, R. and Baltimore, D., 1986, *Cell*, 46:705–716). This factor has been shown to bind to DNA regulatory regions of certain cytokine genes (Leonardo, M. and Baltimore, D., 1989, *Cell*, 58:227–229). Various agents cause the induction of nuclear NF-$\kappa$B DNA-binding activity (Sen and Baltimore, supra). It is thus thought that NF-$\kappa$B is a transcriptional regulator of gene expression for various cytokine genes. It would therefore be desirable to identify molecules that inhibit the effects of NF-$\kappa$B since these would be useful to regulate the effects of cytokines in the inflammatory response.

It has recently been shown that NF-$\kappa$B is associated with a 36 kD protein termed I$\kappa$B (Baeurle, P. and Baltimore, D., 1988, *Cell*, 53:211–217; Baeurle, P. and Baltimore, D., 1988, *Science*, 243:540–546). NF-$\kappa$B consists of proteins having molecular weights of 50 and 65 kD. I$\kappa$B binds to the 65 kD subunit (Baeurle, P. and Baltimore, D., 1989, *Genes and Development*, 3:1689–1698). Finally, recent experimental evidence shows that phosphorylation of I$\kappa$B blocks its inhibitory effect on DNA binding activity of NF-$\kappa$B. This is consistent with the observation that protein kinases activate NF-$\kappa$B DNA binding activity in vitro (Ghosh, S. and Baltimore, D., 1990, *Nature*, 344:678–682).

Because of the importance of I$\kappa$B in regulating gene expression, it will be appreciated that the purification, cloning, and expression of this molecule will make available assays for identification of regulators of NF-$\kappa$B and I$\kappa$B that will have significant medical applications.

SUMMARY OF THE INVENTION

One aspect of the invention described herein consists of a description of a protein that inhibits transcriptional activation by NF-$\kappa$B that has an approximate molecular weight of 34–38 kD.

A second aspect of the invention is the description of a cDNA sequence that encodes a protein that inhibits transcriptional activation by NF-$\kappa$B that has an approximate molecular weight of 34–36 kD.

A third aspect of the invention is a description of methods for cloning and expressing a 34 kD transcriptional activation inhibitor.

A fourth aspect of the invention is a method for identifying medicaments using I$\kappa$B that are useful for controlling diseases resulting from undesirable gene expression.

A fifth aspect of the invention is a method for identifying medicaments that enhance immune responses by their ability to block the effects of I$\kappa$B.

A sixth aspect of the invention is the identification of transcriptional activator inhibitors having properties similar to the instantly described I$\kappa$B, and methods of using such inhibitors to identify medicaments that would be useful to treat diseases resulting from undesirable gene expression.

A seventh aspect of the invention is a description of diagnostic procedures for detecting diseases as a function of IκB expression.

These and other aspects of the invention will become more fully appreciated upon a complete consideration of the invention described below.

BRIEF DESCRIPTION OF THE DRAWINGS

FIG. 1 shows the cDNA sequence of MAD-3(SEQ ID NO:16).

FIG. 2 shows the cDNA sequence of IκB (SEQ ID NO:17), and the deduced protein sequence based thereon (SEQ ID NO:18). The 1.6 kb size of the clone is close to that predicted from the transcript size on Northern analysis. The consensus tyrosine phosphorylation site and the possible PI-3 kinase binding domain is underlined, the predicted PKC phosphorylation site is overlined and the three ATTTA (SEQ ID NO:1) motifs are underlined and typed in bold. The ankyrin repeat domain (Lux et al., 1990, *Nature,* 144:36–42) is typed in bold.

FIG. 3 shows a Kyte-Doolittle hydrophilicity/hydrophobicity plot. The five ankyrin repeats are overlined and each repeat is marked. The predicted PI-3 kinase binding domain and the putative PKC kinase target sequences are also overlined.

FIG. 4A shows in vitro transcribed IκB mRNA translates a 36–38 kD protein with properties of IκB. 10% SDS polyacrylamide gel analyzing reticulocyte lysates programmed with in vitro transcribed IκB mRNA (lane 1, WT) or with IκB mRNA transcribed from an AccI digested plasmid (lane 2, Δ). Protein was labelled with $^{35}$S-methionine. The mobilities of prestained molecular weight markers are shown.

FIG. 4B shows gel mobility shift analyzing programmed reticulocyte lysates and nuclear extracts of PMA and PHA treated Jurkat T-cells. For all lanes the Class I MHC enhancer probe was used. The following protein sources were used: nuclear extracts of stimulated Jurkat T-cells (lane 1), Jurkat extracts plus IκB programmed lysates (lane 2, WT), Jurkat extracts plus lysates translated with mRNA from the AccI-deleted construct (lane 3, Δ), Jurkat extracts plus mock translated reticulocyte lysates alone (lane 5, MT). The large arrow indicates the mobility of the NF-κB/DNA complex and the small arrow indicates the mobility of the KBF1/DNA complex.

DETAILED DESCRIPTION OF THE INVENTION

Figures 4C, 6:
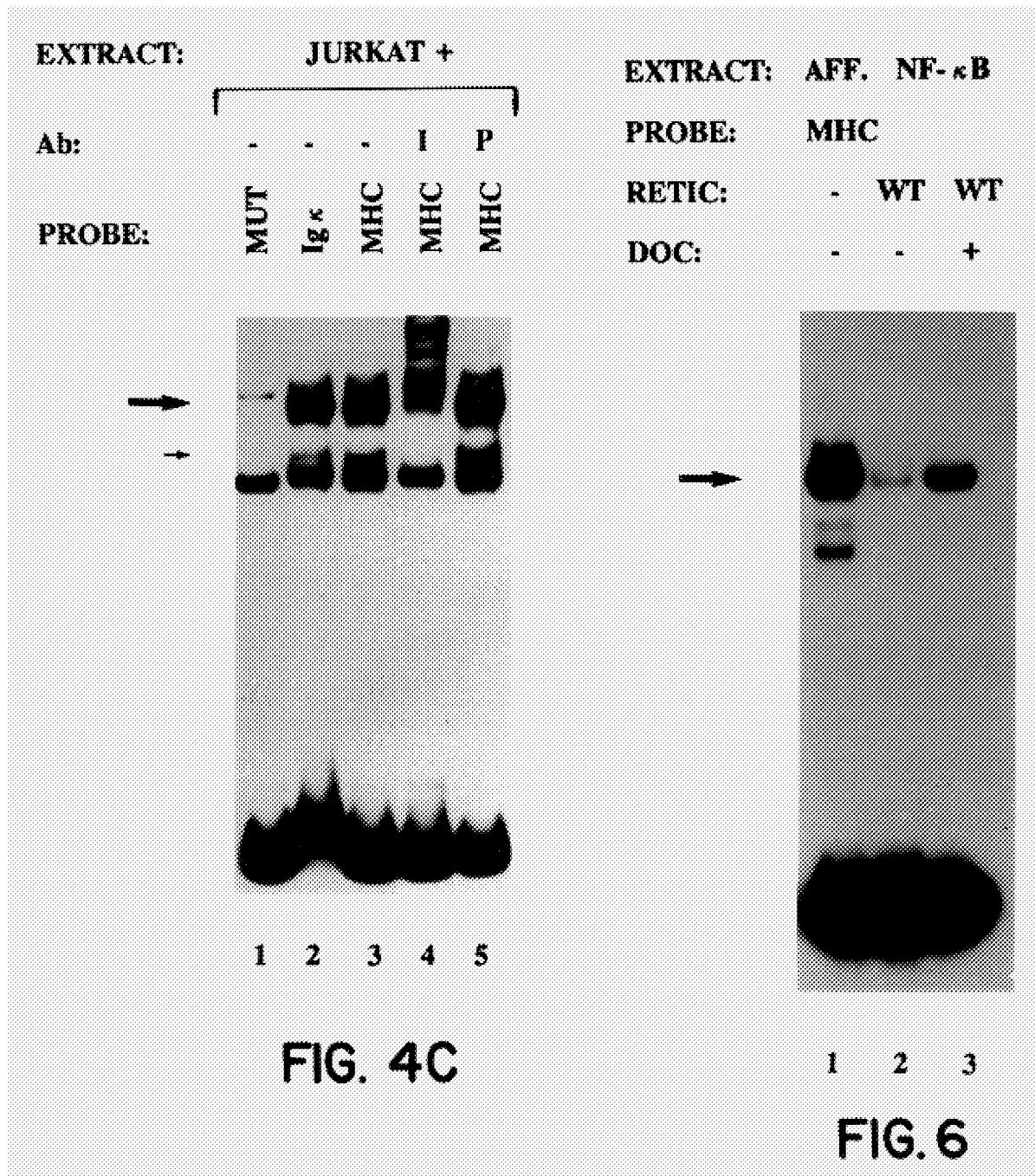
FIG. 4C shows gel mobility shift assay characterizing the nuclear extracts of the stimulated Jurkat T-cells. The following protein sources were used: extracts of stimulated Jurkat T-cells (lanes 1–5), plus either antiserum to the p50 DNA-binding subunit of NF-κB (lane 4, I indicates immune antiserum) or pre-immune (P) serum (lane 5). The DNA probes are as indicated above the figure: MUT (MHC double point mutant probe), Igκ (immunoglolublin kappa), and MHC (Class I MHC enhancer probe). The large arrow indicates the mobility of the NF-κB/DNA complex and the small arrow indicates the mobility of the KBF1/DNA complex.
FIG. 6 shows deoxycholate releases NF-κB DNA-binding activity from the IκB inhibition. Gel mobility shift using the Class I MHC enhancer probe with the following binding conditions: DNA-affinity purified NF-κB (lanes 1–3), plus IκB programmed lysates (lanes 2 and 3). Following incubation of the purified NF-κB with the IκB programmed extract, DOC was added followed by NP40 (lane 3). The arrow indicates the mobility of the NF-κB/DNA complex.

The invention described herein draws on previously published work and pending patent applications. By way of example, such work consists of scientific papers, patents or pending patent applications. All of these publications and applications, cited previously or below are hereby incorporated by reference.

The present invention concerns the isolation, identification, cloning, and expression of a particular factor, hereinafter referred to as NF-κB transcriptional activator inhibitor factor, or IκB. The inhibitor has been characterized with respect to certain of its molecular and chemical properties. Each of these will be discussed separately below.

Before discussing the subject invention IκB inhibitor, it is important to be aware that the inhibitor described herein consists of proteinaceous material having a defined chemical structure. However, the precise structure of the inhibitor depends on a number of factors, particularly chemical modifications known to occur to proteins. For example, since all proteins contain ionizable amino and carboxyl groups it is, of course, apparent that the inhibitor may be obtained in acidic or basic salt form, or in neutral form. It is further apparent, that the primary amino acid sequence may be augmented by derivatization using sugar molecules (glycosylation) or by other chemical derivatizations involving covalent, or ionic attachment to the inhibitor with, for example, lipids, phosphate, acetyl groups and the like, often occurring through association with saccharides. These modifications may occur in vitro. or in vivo, the latter being performed by a host cell through post-translational processing systems. It will be understood that such modifications, regardless of how they occur, are intended to come within the definition of the IκB inhibitor so long as the activity of the protein, as defined below, is not destroyed. It is to be expected, of course, that such modifications may quantitatively or qualitatively increase or decrease the biological activity of the molecule, and such chemically modified molecules are also intended to come within the scope of the invention.

"Cells" or "recombinant host" or "host cells" are often used interchangeably as will be clear from the context. These terms include the immediate subject cell, and, of course, the progeny thereof. It is understood that not all progeny are exactly identical to the parental cell, due to chance mutations or differences in environment.

As used herein the term "transformed" in describing host cell cultures denotes a cell that has been genetically engineered to produce a heterologous protein that possesses the activity of the native protein. Examples of transformed cells are described in the examples of this application. Bacteria are preferred microorganisms for producing the protein. Synthetic protein may also be made by suitable transformed yeast and mammalian host cells.

"Operably linked" refers to juxtaposition such that the normal function of the components can be performed. Thus, a coding sequence "operably linked" to control sequences refers to a configuration wherein the coding sequence can be expressed under the control of these sequences.

"Control sequences" refers to DNA sequences necessary for the expression of an operably linked coding sequence in a particular host organism. The control sequences which are suitable for procaryotes, for example, include a promoter, optionally an operator sequence, a ribosome binding site, and possibly, other as yet poorly understood, sequences. Eucaryotic cells are known to utilize promoters, polyadenylation signals, and enhancers.

"Expression system" refers to DNA sequences containing a desired coding sequence and control sequences in operable linkage, so that hosts transformed with these sequences are capable of producing the encoded proteins. In order to effect transformation, the expression system may be included on a vector, however, the relevant DNA may then also be integrated into the host chromosome.

As used herein, the term "pharmaceutically acceptable" refers to a carrier medium which does not interfere with the effectiveness of the biological activity of the active ingredients and which is not toxic to the hosts to which it is administered. The administration(s) may take place by any suitable technique, including subcutaneous and parenteral administration, preferably parenteral. Examples of parenteral administration include intravenous, intraarterial, intramuscular, and intraperitoneal, with intravenous being preferred.

Finally, it is important to note that while the activity of the inhibitor IκB has been discussed as applied to regulating the transcriptional activity of NF-κB on the expression of genes involved in the inhibitory response or viral infection, it will be appreciated that its scope of inhibitory activity is wider as indicated by the presence of NF-κB in numerous cell lines not involved in inflammation or vial infection. Thus, as to the expression of these genes, IκB can be expected to be useful to identify inhibitors or stimulators of their expression as well.

I. Identification of a cDNA Sequence that Encodes IκB

A. General Cloning Techniques:

Establishing a cDNA library containing the cDNA sequence that encodes a truncated cytokine inhibitor, identification of the cDNA sequence, and subcloning and expressing the sequence makes use of numerous methods known to the skilled practitioner. A general description of the methods and materials used is presented here for the convenience of the reader. More specifically, construction of suitable vectors containing the desired cytokine coding sequence employs standard ligation and restriction methods wherein isolated vectors, DNA sequences, or synthesized oligonucleotides are cleaved, tailored, and religated in the form desired.

Site specific DNA cleavage is performed by treating with suitable restriction enzyme(s) under conditions which are generally understood in the art, and the particulars of which are specified by the manufacturer of these commercially available restriction enzymes. See, e.g., New England Biolabs, Product Catalog. In general, about 1 μg of plasmid or DNA sequence is cleaved by one unit of enzyme in about 20 μl of buffer solution. In the examples herein, typically, an excess of restriction enzyme is used to insure complete digestion of the DNA substrate. Incubation times of about one hour to two hours at about 37° C. are workable, although variations can be tolerated After each incubation, protein is removed by extraction with phenol/chloroform, and may be followed by ether extraction, and the nucleic acid recovered form aqueous fractions by precipitation with ethanol followed by chromatography using a Sephadex G-50 spin column. If desired, size separation of the cleaved fragments may be perfomed by polyacrylamide gel or agarose gel electrophoresis using standard techniques. A general description of size separations is found in *Methods in Enzymology*, 1980, 65:499–560.

Restriction cleaved fragments may be blunt ended by treating with the large fragment of *E. coli* DNA polymerase I, that is, the Klenow fragment, in the presence of the four deoxynucleotide triphosphates (dNTPs) using incubation times of about 15 to 25 minutes at 20° to 25° C. in 50 mM Tris pH 7.6, 50 mM NaCl, 6 mM MgCl$_2$, 6 mM DTT and 10 mM dNTPs. After treatment with Klenow, the mixture is extracted with phenol/chloroform and ethanol precipitated. Treatment under appropriate conditions with S1 nuclease results in hydrolysis of single-stranded portions.

Ligations are performed in 15–30 μl volumes under the following standard conditions and temperatures: 20 mM Tris-Cl pH 7.5, 10 mM MgCl$_2$, 10 mM DTT, 33 μg/ml BSA, 10 mM–50 mM NaCl, and 1 mM ATP, 0.3–0.6 (Weiss) units T4 DNA ligase at 14° C. for "sticky end" ligation, or for "blunt end" ligations 1 mM ATP was used, and 0.3–0.6 (Weiss) units T4 ligase. Intermolecular "sticky end" ligations are usually performed at 33–100 μg/ml total DNA concentration. In blunt end ligations, the total DNA concentration of the ends is about 1 μM.

In vector construction employing "vector fragments," the vector fragment is commonly treated with bacterial alkaline phosphatase (BAP) in order to remove the 5' phosphate and prevent religation of the vector. BAP digestions are conducted at pH 8 in approximately 150 mM Tris, in the presence of $Na^+$ and $Mg^{+2}$ using about 1 unit of BAP per µg of vector at 60° C. for about 1 hour. Nucleic acid fragments are recovered by extracting the preparation with phenol/ chloroform, followed by ethanol precipitation. Alternatively, religation can be prevented in vectors which have been double digested by additional restriction enzyme digestion of the unwanted fragments.

In the constructions set forth below, correct ligations are confirmed by first transforming the appropriate *E. coli* strain with the ligation mixture. Successful transformants are selected by resistance to ampicillin, tetracycline or other antibiotics, or using other markers depending on the mode of plasmid construction, as is understood in the art. Miniprep DNA can be prepared from the transformants by the method of D. Ish-Howowicz et al., 1981, *Nucleic Acids Res.,* 9:2989 and analyzed by restriction and/or sequenced by the dideoxy method of F. Sanger et al., 1977, *PNAS (USA),* 74:5463 as further described by Messing et al., 1981, *Nucleic Acids Res.,* 9:309, or by the method of Maxam et al., 1980, *Methods in Enzymology,* 65:499.

Host strains used in cloning in M13 consists of *E. coli* strains susceptible to phage infection, such as *E. coli* K12 strain DG98 are employed The DG98 strain has been deposited with ATCC Jul. 13, 1984 and has Accession No. 1965.

Depending on the host cell used, transformation is done using standard techniques appropriate to such cells. The calcium treatment employing calcium chloride, as described by Cohen, S. N. et al., 1972, *PNAS (USA)* 69:2:2110, and modifications as described by Hanahan, D., 1983, *J. Mol. Biol.,* 166:557–580 are used for procaryotes or other cells which contain substantial cell wall barriers. Infection with *Agrobacterium tumefaciens* (Shaw et al., 1983, *Gene* 23:315) is used for certain plant cells. Transformations into yeast are carried out according to the method of Van Solingen et al., 1977, *J. Bacterial* 130:946 and Hsiao et al., 1979, *PNAS (USA)* 76:3829.

Several transfection techniques are available for mammalian cells without such cell walls. The calcium phosphate precipitation method of Graham and van der Eb, 1978, *Virology,* 52:546 is one method. Transfection can be carried out using a modification (Wang et al., 1985, *Science* 228:149) of the calcium phosphate co-precipitation technique. Another transfection technique involves the use of DEAE-dextran (Sompayrac, L. M. et al., 1981, *PNAS (USA),* 78:7575–7578). Alternatively, Lipofection refers to a transfection method which uses a lipid matrix to transport plasmid DNA into the host cell. The lipid matrix referred to as Lipofectin Reagent is available from BRL.

Synthetic oligonucleotides are prepared by the triester method of Matteucci et al., 1981, *J. Am Chem. Soc.* 103:3185 or using commercially available automated oligonucleotide synthesizers. Kinasing of single strands prior to annealing or for labeling is achieved using an excess, e.g., approximately 10 units of polynucleotide kinase to 0.1 mmole substrate in the presence of 50 mM Tris, pH 7.6, 10 MM $MgCl_2$, 5 mM dithiothreitol, 1–2 mM ATP, 1.7 pmoles $^{32}$P-ATP (2.9 mCi/mmole), 0.1 mM spermidine, 0.1 mM EDTA.

A specific nucleic acid sequence may be cloned into a vector by using primers to amplify the sequence which contain restriction sites on their non-complementary ends according to the general methods as disclosed in U.S. Pat. No. 4,683,195, issued Jul. 28, 1987, U.S. Pat. No. 4,683,202, issued Jul. 28, 1987, and U.S. Pat. No. 4,800,159, issued Jan. 24, 1989 the latter of which is incorporated herein by reference in its entirety. A modification of this procedure involving the use of the heat stable *Thermus aquaticus* (Taq) DNA polymerase has been described and characterized in European Patent Publication No. 258,017, published Mar. 2, 1988 incorporated herein by reference in its entirety. Also useful is the Thermal Cycler instrument (Perkin-Elmer-Cetus) which has been described in European Patent Publication No. 236,069, published Sep. 9, 1987 also incorporated herein by reference in its entirety.

Generally, the nucleic acid sequence to be cloned is treated with one oligonucleotide primer for each strand and an extension product of each primer is synthesized which is complementary to each nucleic acid strand. An alternative to the use of plasmid DNAs encoding the lymphokines of interest as template for polymerase chain reaction (hereinafter referred to as PCR) is the use of RNA from any cell producing these lymphokines as template for PCR as described in U.S. Pat. No. 4,800,159. If RNA is the available starting material, the extension product synthesized from one primer when separated from its complement can serve as template for synthesized of the extension product of the other primer. As previously mentioned, each primer contains a restriction site on its 5' end which is the same as or different from the restriction site on the other primer. After sufficient amplification has occurred the amplification products are treated with the appropriate restriction enzyme(s) to obtain cleaved products in a restriction digest. The desired fragment to be cloned is then isolated and ligated into the appropriate cloning vector.

For portions of vectors derived from IκB cDNA or genomic DNA which require sequence modifications, site-specific primer directed mutagenesis is used. This technique is now standard in the art, and is conducted using a primer synthetic oligonucleotide complementary to a single stranded phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form; 50% will have the original sequence. The plaques are transferred to nitrocellulose filters and the "lifts" hybridized with kinased synthetic primer at a temperature which permits hybridization of an exact match, but at which the mismatches with the original strand are sufficient to prevent hybridization. Plaques which hybridize with the probe are then picked and cultured, and the DNA is recovered. Details of site specific mutation procedures are described below in specific examples.

In the constructions set forth below, correct ligations for plasmid construction are confirmed by first transforming *E. coli* strain MM294, or other suitable host, with the ligation mixture. Successful transformants are selected by ampicillin, tetracycline or other antibiotic resistance or using other markers, depending on the mode of plasmid construction, as is understood in the art. Further screening of transformants is possible using the technique of colony hybridization essentially as described in Maniatis, T. et al. (supra:312–328). Briefly, colonies are lifted onto nitrocellulose filters and sequentially placed on each of four Whatman filters each saturated with one of the following solutions: (1) in 10% SDS; (2) 0.5M NaOH/1M NaCl; (3) 1.5M NaCl, 1.5M Tris pH 8.0, (4) 2× SSC for approximately 5 minutes each. After cell lysis and binding the DNA, filters were prehybridized for 0.5 to 1 hour at 42° C. in hybridization buffer containing 30% formamide followed by hybridization for 1–2 hrs at 42° C. Filters were washed three times in 2× SSC and 0.1% SDS until background was reduced.

Plasmids from the transformants are then prepared according to the method of Clewell et al., 1969, *PNAS (USA)* 62:1159, optionally following chloramphenicol amplification (Clewell, 1972, *J. Bacterial* 110:667). The isolated DNA is analyzed by restriction and/or sequenced by the dideoxy method of Sanger et al., 1977, *PNAS (USA)*, 74:5463 as further described by Messing et al., 1981, *Nucleic Acids Res.* 2:309, or by the method of Maxam et al., 1980, *Methods in Enzymology* 65:499.

The expression of DNA that encodes IκB inhibitor can be carried out in a wide variety of cell types. Procaryotes most frequently are represented by various strains of *E. coli*. However, other microbial strains may also be used, such as bacilli, for example, *Bacillus subtilis*, various species of Pseudomonas, or other bacterial strains. In such procaryotic systems, plasmid vectors which contain replication sites and control sequences derived from a species compatible with the host are used. For example, *E. coli* is typically transformed using derivatives of pBR322, a plasmid derived from an *E. coli* species by Bolivar et al., 1977, *Gene* 2:95. pBR322 contains genes for ampicillin and tetracycline resistance, and thus provides additional markers which can be either retained or destroyed in constructing the desired vector. Commonly used procaryotic control sequences, which are defined herein to include promoters for transcription initiation, optionally with an operator, along with ribosome binding site sequences, include such commonly used promoters as the beta-lactamase (penicillinase) and lactose (lac) promoter systems (Chang et al., 1977, *Nature* 198:1056), the tryptophan (trp) promoter system (Goeddel et al., 1980, *Nucleic Acids Res.* 8:4057) and the lambda derived $P_L$ promoter (Shimatake et al., 1981, *Nature* 292:128), and N-gene ribosome binding site, which has been made useful as a portable control cassette, U.S. Pat. No. 4,711,845, issued Dec. 8, 1987 and incorporated herein by reference in its entirety, which comprises a first DNA sequence that is the $P_L$ promoter operably linked to a second DNA sequence corresponding to the $N_{RBS}$ upstream of a third DNA sequence having at least one restriction site that permits cleavage within 6 bp 3' of the $N_{RBS}$ sequence. U.S. Pat. No. 4,666,848 issued May 19, 1987 and incorporated herein by reference in its entirety discloses additional vectors with enhanced expression capabilities. Also useful is the phosphatase A (phoA) system described by Chang et al., in European Patent Publication No. 196,864, published Oct. 8, 1986, incorporated herein by reference. However, any available promoter system compatible with procaryotes can be used.

In addition to bacteria, eucaryotic microbes, such as yeast, may also be used as hosts. Laboratory strains of *Saccharomyces cerevisiae*, Baker's yeast, are most used, although a number of other strains are commonly available. While vectors employing the 2 micron origin of replication are illustrated (Broach, 1983, *Meth. Enz.* 101:303; U.S. Pat. No. 4,803,164 incorporated herein by reference in its entirety), other plasmid vectors suitable for yeast expression are known (see, for example, Stinchcomb et al., 1979, *Nature* 282:39, Tschempe et al., 1980, *Gene* 10:157 and Clarke et al., 1983, *Meth. Enz.* 101:300). Control sequences for yeast vectors include promoters for the synthesis of glycolytic enzymes (Hess et al., 1968, *J. Adv. Enzyme. Req.* 7:149; Holland et al., 1978, *Biochemistry* 17:4900).

Additional promoters useful in yeast host microorganisms and known in the art include the promoter for 3-phosphoglycerate kinase (Hitzeman et al., 1980, *J. Biol. Chem.* 255: 2073), and those for other glycolytic enzymes, such as glyceraldehyde-3-phosphate dehydrogenase, hexokinase, pyruvate decarboxylase, phosphofructokinase, glucose-6phosphate isomerase, 3-phosphoglycerate mutase, pyruvate kinase, triosephosphate isomerase, phosphoglucose isomerase, and glucokinase. Other promoters, which have the additional advantage of transcription controlled by growth conditions, are the promoter regions for alcohol dehydrogenase 2, isocytochrome C, acid phosphatase, degradative enzymes associated with nitrogen metabolism, and enzymes responsible for maltose and galactose utilization (Holland, supra).

It is also believed that terminator sequences are desirable at the 3' end of the coding sequences. Such terminators are found in the 3' untranslated region following the coding sequences in yeast-derived genes. Many of the vectors illustrated contain control sequences derived from the enolase gene containing plasmid peno46 (Holland et al., 1981, *J. Biol. Chem.* 256:1385) or the LEU2 gene obtained form YEp13 (Broach et al., 1978, *Gene* 8:121); however, any vector containing a yeast compatible promoter, origin of replication and other control sequences is suitable.

It would be possible to express IκB in eucaryotic host cell cultures derived from multicellular organisms. See, for example, *Tissue Culture* Academic Press, Cruz and Patterson, editors (1973). Useful host cell lines include murine myelomas N51, VERO and HeLa cells, and Chinese hamster ovary (CHO) cells. Expression vectors for such cells ordinarily include promoters and control sequences compatible with mammalian cells such as, for example, the commonly used early and late promoters from Simian Virus 40 (SV 40) (Fiers et al., 1978, *Nature*, 273:113) viral promoters such as those derived from polyoma, Adenovirus 2, bovine papilloma virus, or avian sarcoma viruses, or immunoglobulin promoters and heat shock promoters. A system for expressing DNA in mammalian systems using the BPV as a vector is disclosed in U.S. Pat. No. 4,419,446, incorporated herein by reference in its entirety. A modification of this system is described in U.S. Pat. No. 4,601,978, incorporated herein by reference in its entirety. General aspects of mammalian cell host system transformations have been described by Axel in U.S. Pat. No. 4,399,216 issued Aug. 16, 1983. Also useful is gene amplification in eucaryotic cells as described by Ringold in U.S. Pat. No. 4,656, 134, issued Apr. 7, 1987, incorporated herein by reference in its entirety. It now appears also that "enhancer" regions are important in optimizing expression; these are, generally, sequences found upstream of the promoter region. Origins of replication may be obtained, if needed, from viral sources. However, integration into the chromosome is a common mechanism for DNA replication in eukaryotes.

Plant cells are also now available as hosts, and control sequence compatible with plant cells such as the nopaline synthase promoter and polyadenylation signal sequences (Depicker et al., 1982, *J. Mol. Appl. Gen.*, 1:561) are available. Additionally, methods and vectors for transformation of plant cells have been disclosed in PCT Publication No. WO 85/04899, published Nov. 7, 1985, and incorporated herein by reference in its entirety.

Host strains typically used in cloning, expression and sequencing of recombinant constructs are as follows. For cloning, sequencing, and for expression of construction under control of most bacterial promoters, E. coli strain MM294 obtained from E. coli Genetic Stock Center GCSC #6135, may be used as the host. For expression under control of the $P_L N_{RBS}$ promoter, E. coli strain K12 MC1000λ lysogen, $N_7 N_{53} cI857$ SusP$_{80}$, a strain deposited with the American Type Culture Collection (ATCC 39531), may be used. E. coli DG116, which was deposited with the ATCC (ATCC 53606) on Apr. 7,1987, may also be used.

For M13 phage recombinant, E. coli strains susceptible to phage infection, such as E. coli K12 stain DG98, are employed. The DG98 strain has been deposited with the ATCC (ATCC No. 39768) on Jul. 13, 1984.

Mammalian expression has been accomplished in COS-A2 cells and also can be accomplished in COS-7, and CV-1, hamster and murine cells. Insect cell-based expression can be in *Spodoptera frugiperda*.

B. Establishment of a cDNA Library:

A full length cDNA sequence that encodes the IκB inhibitor may be obtained using molecular biology techniques well known in the art, with the noted exceptions detailed below.

Several procedures are available for identifying the relevant cDNA sequences. The preferred procedure is to generate a library using RNA isolated from adherent monocytes, but a library can be generated from virtually any source of biological material that expresses the inhibitor, indeed, cDNA libraries can even be purchased commercially. Monocytes are the preferred starting material because adherence to an appropriate surface induces the expression of the IκB inhibitor.

An illustrative procedure for making a cDNA library containing the inhibitor sequences consists of isolating total cytoplasmic RNA from a suitable starting material, and further isolating messenger RNA therefrom. The latter can be further fractionated into Poly (A+) messenger RNA, which in turn may be fractionated further still into Poly (A+) messenger RNA fractions containing cytokine inhibitor messenger RNA. The messenger RNA can then be reverse transcribed and cloned into a suitable vector to form the cDNA library.

More specifically, the starting material (i.e., tissue, cells) is washed with phosphate buffered saline, and a non-ionic detergent, such as ethylene oxide, polymer type (NP40) is added in an amount to lyse the cellular, but not nuclear membranes, generally about 0.3%. Nuclei can then be removed by centrifugation at 1,000× g for 10 minutes. The post-nuclear supernatant is added to an equal volume of TE (10 mM Tris, 1 mM ethylenediaminetetraacetic acid (EDTA), pH 7.5) saturated phenol/chloroform (1:1) containing 0.5% sodium dodecyl sulfate (SDS) and 10 mM EDTA. The supernatant is re-extracted 4 times and phase separated by centrifugation at 2,000× g for 120 minutes. The RNA is precipitated by adjusting the samples to 0.25M NaCl, adding 2 volumes of 100% ethanol and storing at −20° C. The RNA is then pelleted at 5,000× g for 30 minutes, washed with 70% and 100% ethanol, and dried. This represents the total cytoplasmic RNA.

Alternatively, total cytoplasmic RNA may be isolated using the guanidine isothiocyanate-cesium chloride method as described by Chirgwin et al., 1979, *Biochemistry* 18:5294.

Polyadenylated (Poly A+) messenger RNA (mRNA) can be obtained from the total cytoplasmic RNA by chromatography on oligo (dT) cellulose (J. Aviv et al., 1972, *PNAS*, 69:1408–1412). The RNA is dissolved in ETS (10 mM Tris, 1 mM EDTA, 0.5% SDS, pH 7.5) at a concentration of 2 mg/ml. This solution is heated to 65° C. for 5 minutes, then quickly chilled to 4° C. After bringing the RNA solution to room temperature, it is adjusted to 0.4M NaCl and slowly passed through an oligo (dT) cellulose column previously equilibrated with binding buffer (500 mM NaCl, 10 mM Tris, 1 mM EDTA, pH 7.5). The flow-through is passed over the column twice more, and the column washed with 10 volumes of binding buffer. Poly (A+) mRNA is eluted with aliquots of ETS, extract once with TE-saturated phenol chloroform and precipitated by the addition of NaCl to 0.2M and 2 volumes of 100% ethanol. The RNA is reprecipitated twice, washed once in 70% and then 100% ethanol prior to drying. The poly (A+) mRNA can then be used to construct a cDNA library.

cDNA can be made from the enriched mRNA fraction using oligo (dT) priming of the poly A tails and AMV reverse transcriptase employing the method of H. Okayama et al., 1983, *Mol. Cell Biol.* 3:280, incorporated herein by reference.

Other methods of preparing cDNA libraries are, of course, well known in the art. One, now classical, method uses oligo (dT) primer, reverse transcriptase, tailing of the double stranded cDNA with poly (dG) and annealing into a suitable vector, such as pBR322 or a derivative thereof, which has been cleaved at the desired restriction site and tailed with poly (dC). A detailed description of this alternate method is found, for example, in U.S. Ser. No. 564,224, filed Dec. 20, 1983, and assigned to the same assignee, incorporated herein by reference.

A preferred method by which a cDNA clone that encodes the IκB inhibitor may be identified is to employ a cDNA library that is produced using RNA obtained from induced monocytes, and to detect individual clones that differentially hybridize to cDNA probes produced using RNA from induced and uninduced monocytes. Clones that preferentially hybridize to cDNA probes produced from induced but not uninduced monocyte RNA will contain cDNA that encodes the cytokine inhibitor of the instant invention.

cDNA inserts may be sequenced using known techniques. The preferred technique is to subclone the inserts into an appropriate vector, an exemplary vector being pGEM blue (Promega Biotec. Madison, Wis. Corp.), and sequence the double stranded DNA using the dideoxy chain termination method described by Sanger et al., 1977, *PNAS (USA)*, 74:5463. Sequencing is conveniently performed using commercially available kits, preferably the Sequenase sequencing kit produced by United States Biochemical Co. Cleveland, Ohio, and using suitable primers, such as T7 and SP6 obtainable from Promega Biotec. Madison, Wis., and sequence specific primers.

C. IκB Assays:

To confirm that a cDNA sequence does encode IκB, gel mobility shift assays may be performed. The assay is based on the observation that NF-κB binds to a defined DNA in the absence but not the presence of IκB. The assay consists of detecting the effect of IκB, produced by reticulocyte translation, on the binding of NF-κB to a Class I MHC enhancer sequence, TGGGGATTCCCCA (SEQ ID NO: 2). Previously, this enhancer sequence has been demonstrated to bind to NF-κB (Baldwin, and Sharp, P., 1988 *PNAS (USA)*, 85:723–727). The source of NF-κB in the assays may be nuclear extracts of a variety of cell types, but the preferred source is mitogen and phorbol ester induced Jurkat T-cells. The induction NF-κB in this cell line is well documented (Nabel, G. and Baltimore, D., 1987, *Nature,* 326:711–713).

The gel mobility shift assay is conducted by incubating appropriate amounts of the following materials: nuclear extracts obtained from Jurkat cells and/or rabbit reticulocyte lysates, either with IκB mRNA or without, and an appropriate labelled MHC enhancer binding probe. The reaction is conducted in a buffered solution containing appropriate amounts of the following: sodium chloride, EDTA, DTT, poly dI-dC (Pharmacia) and glycerol. The reaction is preferably conducted at room temperature for about 15 minutes and then subjected to electrophoresis on a non-denaturing 5% polyacrylamide gel using a Tris/glycine/EDTA buffer as described by Baldwin, A., 1990, *DNA & Protein Eng. Tech.*, 2:73–76. The gel is dried and autoradiographed overnight using known techniques in the art.

Using the above described gel mobility shift assay, cDNA clones that encode IκB can be identified by their ability to eliminate or reduce the binding of NF-κB to the MHC enhancer DNA binding probe.

Further tests may be conducted to confirm that a cDNA sequence encodes IκB and not a molecule that non-specifically binds to a variety of DNA enhancer binding proteins. These tests may be conducted using the gel mobility shift assay essentially as described above, but with the substitution of a different DNA enhancer sequence and/or a different transcription regulator for NF-κB. A variety of such proteins were tested including KBF1, MLTF, Oct-1 or H2T1.

It will be appreciated by those skilled in the art, that knowledge of the DNA sequence that encodes IκB enables the synthesis of nucleotide probes that can be used to measure the expression of IκB in biological systems using techniques known in the art. This in turn will facilitate the identification of chemicals that induce or suppress the expression of IκB. The identification of such chemicals would have value as medicaments, while a determination of the levels of IκB expression would have diagnostic value.

Having described what the applicants believe their invention to be, the following examples are presented to illustrate the invention, and are not to be construed as limiting the scope of the invention.

EXAMPLE 1

Cloning of IκB

The preferred procedure for constructing a cDNA library that contains a cDNA sequence that encodes the IκB inhibitor is to generate the library from RNA isolated from adherent monocytes. These procedures are described by Sporn, S. A. et al., *J. of Immunol*, 1990, 144:4434. Briefly, the starting material consists of adherent monocytes. Monocytes may be obtained fresh from human volunteers, or from the American Red Cross. In both instances, the monocytes are isolated from whole blood initially in the form of a mononuclear cell fraction prepared by Ficoll-Hypaque sedimentation methods known in the art. Boyun, A., 1968, *Scandinavian J. of Clinical Lab. Invest.*, 21:77. The monocytes are then isolated from the mononuclear fraction by density fractionation using Percoll. Ulmer, A. J., and Flad, D. H., 1979, *J. of Immunological Methods*, 30:1. Alternatively, monocytes may be isolated by plating them onto plastic tissue culture dishes as described by Eierman, D. F., et al., 1989, *J. of Immunology*, 142:1970.

The monocytes are induced to express of the IκB inhibitor by seeding the monocytes onto tissue culture plates or collagen coated tissue culture plates as generally described by Eierman, D. F., et al., 1989, *J. Immunol.*, 142:1970. A variety of materials may be used to coat the tissue culture plates to effect monocyte adherence, and include fibronectin. Briefly, 100 mm tissue culture plates are coated with 100 μg/ml of human fibronectin in phosphate buffered saline (PBS) for 45 minutes at 37° C. Excess fibronectin is removed by washing the plates with PBS and the plates air dried before use. Monocytes are seeded onto the plates and are adherent to the tissue culture plates for at least the 30 minutes prior to the total RNA being extracted therefrom. The monocytes are cultured in RPM 1640 media containing 20 μg/ml of gentamicin sulfate at 37° C. in an atmosphere of 95% air/5%$CO_2$. Generally, about $1-2 \times 10^7$ cells are seeded per 100 mm dish Next, adherent monocytes are lysed after removing the culture medium by adding 3.5 ml of a solution containing 4M guanidinium thiocyanate solution previously prepared by mixing 50 g of Fluka pure grade material with 0.5 g of sodium N-lauroylsarcosine (final concentration 0.5%), 2.5 ml of 1M sodium citrate, pH 7.0 (25 mM), and 0.7 ml of 2-mercaptoethanol (0.1M). The solution is made up to 100 ml with deionized water, and filtered to remove any insoluble material. The pH was adjusted to 7 with 1M NaOH.

Next, the monocyte RNA is separated from the guanidinium thiocyanate homogenate by ultra centrifugation through a dense cushion of cesium chloride. Technical grade cesium chloride is made 5.7M and buffered with 0.1M EDTA, pH 7, or 25 mM sodium acetate or citrate, pH 5. The solution is sterilized with 0.2% diethyl pyrocarbonate, and filtered through a 0.45 μm Millipore filter. The monocyte RNA in the guanidinium thiocyanate is then separated from the guanidinium thiocyanate by ultracentrifugation through the cesium chloride cushion. The RNA pellets that form after the ultracentrifugation are redissolved if necessary by brief heating at 68° C. in a water bath, or by first extracting excess cesium chloride from the RNA pellets with ethanol and drying with nitrogen. RNA isolated in this manner may be used to prepare an appropriate cDNA library.

Total RNA isolated as described above may be used for construction of a cDNA library using those methods described by Watson and Jackson, 1985, *DNA Cloning*, 1:79, "A Practical Approach", (D. M. Glover, ed.), IRL Press, Oxford; and Huynh, et al., 1985, "Constructing and Screening Libraries in Lambda GT10 and Lambda GT11", *DNA Cloning*, 1:49, A Practical Approach, (D. M. Glover, ed.), IRL Press, Oxford. This method entails converting the RNA to double stranded cDNA using AMV reverse transcriptase and the Klenow fragment DNA polymerase 1, as is known in the art. EcoRI linkers were ligated to the double stranded cDNA fragments, size selected and packaged into λ gt 10 vector using a commercially available packaging extract, Gigapack (Stratagene, San Diego, Calif.). This library contained about $5.3 \times 10^6$ recombinants at a frequency of about $7 \times 10^7$ per μg of DNA.

From the library described above, a sub-library was derived by selecting 4,000 clones that do not hybridize to a $^{32}$P-labelled first-strand cDNA probe that was made using RNA obtained from uninduced monocytes.

The sub-library described above was screened by differential hybridization with $^{32}$P-labelled first-stand cDNA probes prepared by reverse transcription of RNA isolated from monocytes that adhere for either 30 minutes or 4 hours, or from controlled non-adherent monocytes. Those plaques which exhibited hybridization with the cDNA probe made from adhered monocytes compared to non-adhered monocytes were selected, and rescreened with the probe. This resulted in the isolation of a 350 base pair fragment termed MAD-3, which represents a partial sequence of IκB. Note that the MAD-3 sequence is nearly identical to bases 783–1117 of the IκB cDNA with the exception that there is an additional triplet, TGA, in MAD-3. The sequence of MAD-3 is shown in FIG. 1. A full length IκB clone was obtained using MAD 3 to probe a second cDNA library made from mRNA isolated from adhered monocytes and neutrophils. The mRNA was reversed transcribed and the cDNA cloned into the pcDNA 1 vector. This vector is available from In Vitrogen Corporation. Screening of this library yielded several full-length clones, and one of these was sequenced.

EXAMPLE 2

DNA Sequence of IκB cDNA inserts were subcloned into the double-stranded vector PGEM blue (Promega Biotec, Madison, Wis.). dscDNA sequencing was performed by the dideoxy chain termination method (as described in Sanger, F. S., et al., 1977, PNAS (USA), 74:5463) by using the Sequenase sequencing kit (United States Biochemical Co., Cleveland, Ohio) with T7 and SP6 primers (Promega), as well as sequence-specific oligonucleotide primers. FIG. 2 shows the cDNA sequence of IκB.

The sequence of IκB shows that it is about 1550 base pairs in length, and extends 94 base pairs 5' of a Kozak consensus sequence for the predicted start site of translation. The 3' untranslated region displays three ATTTA (SEQ ID NO:1) motifs that are associated with rapid turnover of mRNA (Kaput D., et al., 1986, PNAS (USA), 83:1670–1674). The poly A tail begins at the end of the base pair 1550.

The deduced amino acid sequence of IκB is shown in FIG. 2, and is based on the cDNA sequence. The protein would have 317 amino acids, and thus have approximate molecular weight of 34 kD. The molecule is characterized in having three apparent domains. The first, the N-terminal domain, exhibits a 72 amino acid hydrophilic stretch that contains a consensus sequence, DEEYEQMVK (SEQ ID NO: 3), for tyrosine phosphorylation. The second domain, the C-terminal domain, contains a consensus sequence for PKC phosphorylation, RPSTR (SEQ ID NO: 4), and a region rich in PEST (SEQ ID NO: 5) residues, amino acids 264–314 which are associated with rapid protein turnover. The third domain consists of amino acids 74–242, which comprises five tandem repeats of the ankyrin consensus sequence (Lux S. E. et al., 1990, Nature, 344:36–42). FIG. 3 shows a Kyte-Doolittle hydrophilicity/hydrophobicity plot. The five ankyrin repeats are overlined and each repeat is marked. The predicted tyrosine phosphorylation domain and the putative PKC kinase target sequences are also overlined.

EXAMPLE 3

IκB Assays

The IκB DNA sequence in the expression plasmid, pcDNA 1, was used to generate RNA using SP6 RNA polymerase. The RNA was translated in a rabbit reticulocyte lysate mixture in the presence of $^{35}$S-methionine, and the products analyzed on a 10% SDS polyacrylamide gel. As a control, mock translated lysates were run. FIG. 4A shows the results. Since the reticulocyte lysate used for translation contained an endogenous NF-κB-like activity (data not shown), the lysates were depleted for this activity using a DNA affinity matrix specific for NF-κB. These NF-κB-depleted reticulocyte lysates demonstrated virtually no Class I MHC enhancer binding activity (see FIG. 4B, lane 5). The reticulocyte lysates were then used to translate either full length IκB mRNA, or mRNA derived from an AccI digest of the cDNA or were mock translated. AccI cuts the IκB cDNA at the position corresponding to amino acid 167 in the third ankyrin repeat. The in vitro translated products, labelled with $^{35}$S-methionine, were electrophoresed on a 10% SDS polyacrylamide gel. As predicted from the cDNA, the full length IκB mRNA and the mRNA from the AccI-digested plasmid revealed approximately 36 and 22 kD proteins (FIG. 4A, lanes 1 and 2).

Briefly, the reticulocyte translation reaction was conducted as follows. 2 μg of pcDNA1 containing full length IκB cDNA was digested with BamHI or with AccI. The restriction enzyme cuts downstream of the cDNA insert. The reaction digest was phenol/chloroform extracted, ethanol precipitated and used to synthesize RNA in a 100 μl reaction for 1 hour at 37° C. using SP6 RNA polymerase following the conditions recommended by the manufacturer (Boehringer Mannheim). The resulting RNA was extracted twice with phenol/chloroform, ethanol precipitated and redissolved in 20 μl of water. Synthesis of RNA was confirmed by electrophoresis using agarose gels.

However, before conducting the translation reaction, rabbit reticulocyte lysates were first depleted of an endogenous NF-κB-like DNA-binding activity. This was performed by adding 10 μl of lysate to 20 μl of DNA affinity resin previously washed with deionized water. This procedure is described below. The binding reaction was performed, with frequent mixing, for 10 minutes at room temperature. The mixture was pelleted by brief centrifugation in a microfuge and the supernatant was removed for in vitro translation reactions. Next, 4 μl of RNA was used for in vitro translation in a rabbit reticulocyte lysate system obtained from Promega Biotech. The conditions for performing the reaction were those recommended by the manufacturer. The resulting $^{35}$S-methionine labelled products were analyzed on a 10% SDS polyacrylamide gel as described by Laemmli U., 1970, Nature, 227:680–685. The gel was dried and exposed for autoradiography using standard methods.

The DNA affinity resin contained the MHC Class I enhancer sequence TGGGGATTCCCCA (SEQ ID NO: 2), covalently linked to cyanogen bromide activated Sepharose 4B (Sigma). The resin was made and the purification of NF-κB carried out essentially by the method of Kadonaga and Tjian (1986). Nuclear extracts of PMA and PHA stimulated Jurkat T-cells were used for the NF-κB purification. Jurkat nuclear extracts were incubated with the resin for 20 minutes and the NF-κB was eluted with a salt gradient. Only one round of DNA affinity chromatography was performed.

To determine that the IκB cDNA sequence does encode a molecule that binds to NF-κB, gel mobility shift assays were performed. The assay consisted of detecting the binding of IκB produced by reticulocyte translation to NF-κB on acrylamide gels as revealed by binding of a Class I MHC enhancer sequence, TGGGGATTCCCCA (SEQ ID NO: 2). Previously, this enhancer sequence has been demonstrated to bind to NF-κB (Baldwin, and Sharp, P., 1988 PNAS (USA), 85:723–727). The source of NF-κB in the assays was nuclear extracts of mitogen and phorbol ester induced Jurkat T-cells (described below). The induction of NF-κB in this cell line is well documented (Nabel, G. and Baltimore, D., 1987, Nature, 326:711–713), and, furthermore, there is an activity having the properties ascribable to KBF1.

The gel mobility shift assay was conducted as follows. 10 μg of nuclear extracts obtained from Jurkat cells and/or 1 μl of rabbit reticulocyte lysates, either with IκB mRNA or without, and 10,000 counts/minute of N-labelled MHC enhancer binding probe were incubated in 10 mM Tris, pH 7.7, 50 mM sodium chloride, 0.5 mM EDTA, 1 mM DTT, 2 μg poly dI-dC (Pharmacia) and 10% glycerol in a final volume of 20 μl. The reaction was conducted at room temperature for 15 minutes and then subjected to electrophoresis on a nondenaturing 5% polyacrylamide gel using a Tris/glycine/EDTA buffer as described by Baldwin, A., 1990, DNA & Protein Eng. Tech. 2:73–76. Electrophoresis was conducted for approximately 2 hours at 20 mA. The gel was dried and autoradiographed overnight at −70° C. using known techniques in the art.

The DNA/protein complexes indicated by the arrows in FIG. 4 appear by various criteria to be NF-κB and KBF1. Addition of the IκB programmed lysates inhibited the DNA-binding activity associated with the slower NF-κB/DNA complex (indicated by the large arrow, FIG. 4B, lane 2) in the stimulated Jurkat T nuclear extracts and only weakly affected the factor associated with the faster moving KBF1/DNA complex (indicated by the small arrow, FIG. 4B, lane 2). Addition of either lysates programmed with the deleted mRNA or mock translated lysates did not affect either DNA-binding activity (FIG. 4B, lanes 3 and 4).

To further characterize the DNA-binding activities in the nuclear extracts of the PMA and PHA stimulated Jurkat cells, several assays were performed. We first demonstrated that the two activities identified by the arrows are specific for the MHC enhancer probe as they do not interact with a double point mutated probe (FIG. 4C, lane 1). We have previously shown that this mutant probe TGCGGATTC-CCGA (SEQ ID NO: 6) is not bound by NF-κB (Baldwin and Sharp, 1988, above). The factors associated with the slower and faster complexes interact equally well with immunoglobulin kappa and Class I MHC enhancer probes (FIG. 4C, lanes 2 and 3), consistent with these activities being NF-κB and KBF1. Finally, the two DNA/protein complexes are recognized by antibodies against the p50 subunit of NF-κB (FIG. 4C, lane 4) but not by pre-immune serum (FIG. 4C, lane 5). Thus, the IκB protein strongly inhibits an authentic NF-κB activity from stimulated Jurkat T-cells and may inhibit the Jurkat KBF1 activity very weakly.

Nuclear extracts were prepared from Jurkat T-cells using the method of Swick et al.,1989, *Nucleic Acids Res.*, 17:9291–9304. The cells were grown in RPMI 1640 medium containing 10% fetal calf serum. If desired, the cells were stimulated with phytohemagglutinin (PHA) and phorbol 12-myristate 13-acetate (PMA). These were used at final concentrations of 1 μg/ml and 50 ng/ml, respectively.

Figure 5A:
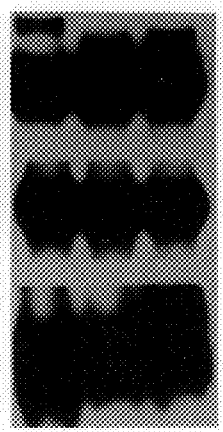
FIG. 5A shows specificity of inhibition of DNA-binding activity by the IκB protein. Gel mobility shift analyzing various DNA-binding activities. The adenovirus MLTF and Oct-1 (OCTA) probes (as indicated) were incubated with nuclear extracts of stimulated Jurkat T-cells (lanes 1–3) plus IκB programmed lysates (lane 2, WT), or plus mock translated lysates (lane 3, MT). The Class I MHC enhancer probe was incubated with a phosphocellulose fraction from HeLa cells (lane 1) containing the DNA-binding activity H2TF1 (Baldwin and Sharp, 1987, *Mol. Cell. Biol.,* 7:305–313), plus IκB programmed lysates (lane 2, WT) or plus mock translated lysates (lane 3, MT).
Figure 5B:
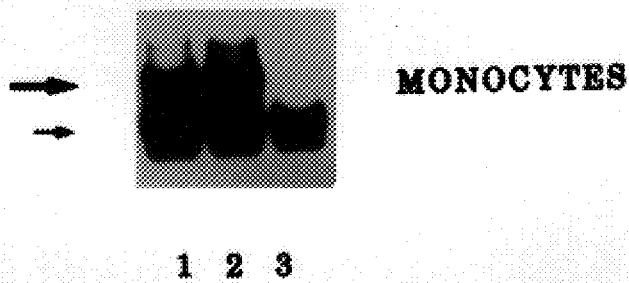
FIG. 5B shows gel mobility shift analyzing NF-κB in nuclear extracts of monocytes. The Class I MHC enhancer probe was incubated with nuclear extracts of freshly isolated monocytes (lane 1). Lane 2 included the addition of mock translated lysates (MT) and lane 3 included the addition of IκB translated lysates (WT). The large arrow indicates the mobility of the NF-κB/DNA complex and the small arrow indicates the mobility of the KBF1/DNA complex.

To demonstrate that the observed inhibition is specific for the NF-κB activity, we analyzed the affect of the IκB protein on other characterized DNA-binding proteins (FIG. 5A). IκB did not inhibit the DNA-binding activity of the major late transcription factor (Carthew et al., 1985, *Cell*, 43:439–448; also known as USF), the Oct-1 factor (Singh, et al., 1986, *Nature*, 319:154–158), or H2TF1, a Class I MHC enhancer binding factor (Baldwin and Sharp, 1987). We next analyzed whether NF-κB from another cell source would be inhibited by the translated IκB protein. NF-κB from nuclear extracts of freshly isolated monocytes was inhibited by the IκB protein, but the KBF1 activity found in these cells was unaffected (FIG. 5B). Both the NF-κB and KBF1 activities in these extracts are recognized by antibodies to the p50 NF-κB subunit. Thus, the IκB protein is highly specific for NF-κB from several cell sources and has little or no effect on KBF1 DNA binding activity (FIGS. 4B and 5B). These results are consistent with the observation that IκB interacts with the 65 kD subunit of NF-κB, which is absent in KBF1 (Kieran et al., 1990, *Cell*, 62:1007–1018). We, therefore, conclude that the IκB translation product specifically inhibits NF-κB DNA -binding activity and does not inhibit the DNA-binding activity of KBF1, MLTF, Oct-1 or H2TF1.

The DNA-binding probes are labelled HindIII-EcoRi digests of pUC plasmids containing oligonucleotides cloned into the polylinker with BamHI restriction ends. The sequence of the Class I MHC enhancer probe is GGCTGG-GATTCCCCATCT (SEQ ID NO: 7) and the mutant MHC probe is GGCTGCGGATTCCCGATCT (SEQ ID NO: 8) (Baldwin and Sharp, 1987), the sequence of the MLTF probe is ACCCGGTCACGTGGCCTACA (SEQ ID NO: 9), the sequence of the Oct-1 probe is ATGCAAAT (SEQ ID NO: 10), and the sequence of the immunoglobulin kappa probe is CAGAGGGACTTTCCGAGA (SEQ ID NO: 11).

Thus, based on the experiments presented above, it is concluded that the cDNA sequence that encodes IκB produces a protein that specifically inhibits NF-κB DNA binding activity, and does not inhibit the activities associated with KBF1, MLTF, Oct-1, 1, or H2TF1.

Another characteristic of IκB is that it can be released from NF-κB with sodium deoxycholate (DOC). Once IκB is released from NF-κB, NF-κB can then bind to DNA. Thus, to further characterize IκB, we treated a reticulocyte lysate programmed with IκB mRNA with sodium deoxycholate, and NP40 and the treated mixture tested in a gel mobility shift assay as described previously. Endogenous NF-κB was removed by DNA affinity chromatography, as described above, to remove endogenous NF-κB/IκB complexes. Similar to crude nuclear extracts of stimulated Jurkat T-cells, (FIG. 4B), the IκB translation product inhibits this partially purified NF-κB (FIG. 6, lane 2).

More specifically, 10 μg of nuclear extracts containing NF-κB was reacted with 1 μl of IκB programmed lysates or mock translated lysates under the binding conditions described above. The reactions were kept at room temperature for 10 minutes followed by the addition of 2 μg of poly dI-dC and 10,000 cpm of radiolabelled DNA probe. The reactions were then loaded onto a 5% polyacrylamide Tris/glycine/EDTA gel and analyzed as described above. For the dissociation reactions, 0.8% sodium deoxycholate was added to the binding reactions (minus poly dI-dC and probe) followed by 1.2% NP40. Poly dI-dC and probe were added and incubated at room temperature for 15 minutes. These reactions were electrophoresed and analyzed as described above. Treatment of the NF-κB/IκB reaction with sodium deoxycholate (DOC) followed by NP40 incubation released NF-κB DNA-binding activity (FIG. 6, lane 3). Thus, the release of NF-κB DNA-binding activity from the reaction is derived from NF-κB/IκB complexes and not from any endogenous NF-κB/IκB in the extract. Since NF-κB DNA-binding activity can be recovered from performed NF-κ/IκB by DOC treatment, we conclude that IκB encodes a protein with properties of IκB.

EXAMPLE 4
Tissue Distribution of IκB

The presence of the IκB inhibitor of the instant invention in various tissues/cells was determined using Northern blot analysis or PCR Northern blot analysis consisted of isolating total RNA from the tissue to be tested using the guanidine isothiocyanate-cesium chloride method as described by Haskill et al., above. Filters were hybridized at 43° C. and washed to a final stringency of 0.2× SSC at 56° C. using IκB as a probe.

PCR analysis was conducted using 1 μg of total RNA isolated as described above, whereby the RNA was converted into first strand DNA using random hexamers as described Kawasaki et al., 1989, Detection of Gene Expression in, *PCR Technology* (ed. Erlich), H. A. (Stockton, N.Y.), pages 89–97. Next, amplification was carried out with a 5'-TCGTCCGCGCCATGTTCCAG (SEQ ID NO: 12) (base pair 85–103) and 3' anti-sense primer GCGGATCACTTC-CATGGTCAG (SEQ ID NO: 13) (base pair 359–379). So that transcript frequencies could be compared from one tissue type to another, dose response curves were determined at the same PCR cycle number, 30, as test samples. Standards included IκB cDNA at various dilutions, as well as RNA isolated from monocytes that had adhered for 4 hours to a substratum that induces IκB expression. NF-κB primers were synthesized using the published sequences of Kieran et al., 1990, Cell, 62:1007–1018. The sense primer was TAGAGCAACCTAAACAGAG (SEQ ID NO: 14) (base pair 316–335) and the anti-sense primer, TCATTCGTGCT-TCCAGTGT (SEQ ID NO: 15) (base pair 629–648).

Figure 7A:
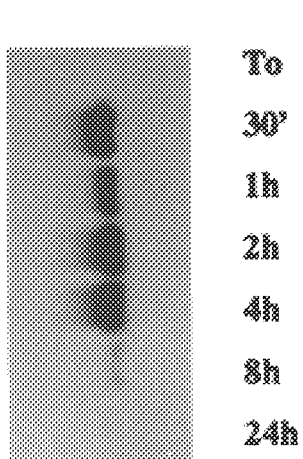
FIG. 7A shows kinetics of induction, substrate specificity, and tissue distribution of IκB mRNA expression. Monocytes isolated by non-adherent techniques were plated on Type IV collagen coated plates and RNA was extracted from adherent cells at the time points indicated and assayed by Northern transfer analysis employing the original IκB cDNA clone insert as probe (Sporn et al., 1990). Times analyzed were freshly isolated monocytes ($T_o$), 30 minutes (30') and 1, 2, 4, and 8 hours post-adhesion to Type IV collagen coated plates. Levels of RNA were normalized by comparing intensity of ethidium bromide-stained 18 and 28s RNA bands.

FIG. 7A shows that IκB is not seen in freshly Percoll-isolated monocytes ($T_0$), but is induced by binding to Type IV collagen.

Figure 7B:
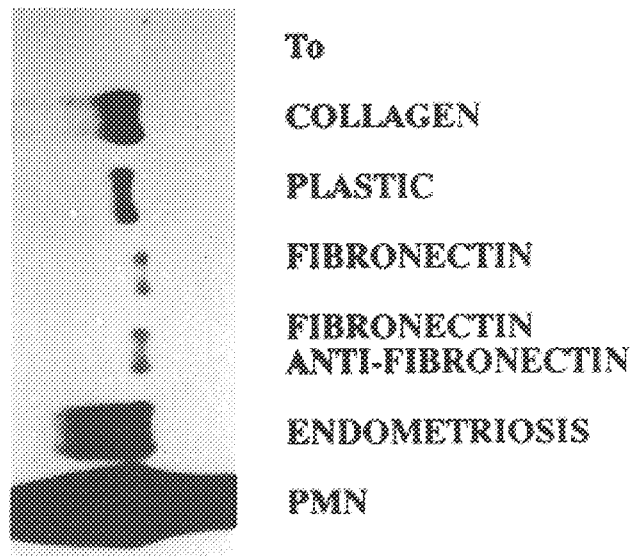
FIG. 7B shows monocytes plated on plastic dishes either uncoated or pre-treated with Type IV collagen, fibronectin, fibronectin complexed with anti-fibronectin (Eierman et al., 1989). RNA was extracted at 4 hours and analyzed by Northern blotting using the IκB probe. RNA from endometiosis-derived inflammatory peritoneal macrophages and freshly isolated neutrophils (PMN) were also analyzed.

Northern analysis revealed that IκB is highly expressed in monocytes adherent to different substrates and in blood neutrophils and is also present in endometriosis associated peritoneal inflammatory macrophages. These results are shown in FIG. 7B.

Figure 7C:
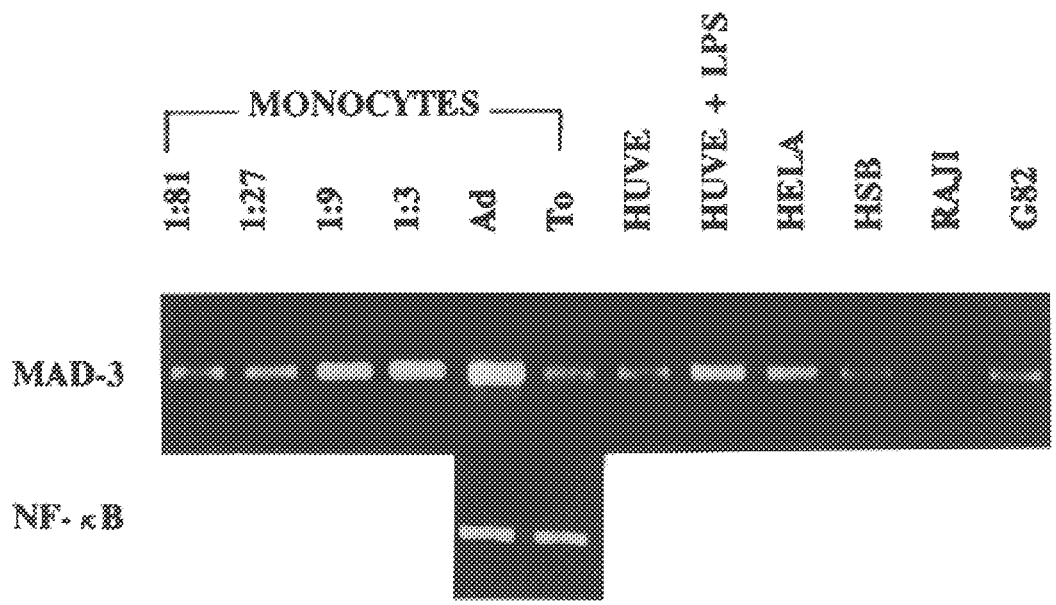
FIG. 7C shows RNA from monocytes and various cell lines were analyzed by semi-quantitative PCR techniques to determine constitutive and inducible levels of IκB mRNA. RNA samples included human umbilical vein endothelium (HUVE) with or without 4 hours stimulation with LPS; HeLa (carcinoma), RAJI (B-cell), HSB (T-cell) or S68 (glioblastoma) cells. Serial dilutions of 4 hours adhered monocyte cDNA was used for quantitative purposes. For comparison, cDNA from fresh monocytes and 4 hours adhered monocytes were examined for expression of the NF-κB transcript.

PCR analysis revealed constitutive expression of IκB mRNA in a number of samples examined (FIG. 7C). This included HSB and RAJI cells, glioblastoma cells, G82, and HUVE cells. The amount of IκB could be increased by activation of HUVE cells by LPS, causing approximately a 9-fold increase in IκB expression. Adherence of HUVE cells caused a 80-fold increase in expression. Expression of NF-κB is also shown for $T_0$ and 4 hour plastic-adherent monocytes. IκB was also observed to be present in several melanoma cell lines, and the level of expression is enhanced 2–3-fold by exposure to PMA, but little or no increase is observed after exposure to IL-2 or TNF (not shown).

EXAMPLE 5
Identification of Medicaments

IκB may be used in a suitable assay format to identify medicaments that enhance or inhibit gene expression. Purified recombinant or naturally occurring IκB may be used in combination with NF-κB to identify chemicals that inhibit the formation of IκB/NF-κB complex formation, or that stabilize the complex once formed. Alternatively, in vitro transcription and translation of IκB can be employed, as discussed below. The materials and methods for carrying out these procedures are described above, and incorporated herein by reference.

Chemicals that inhibit or prevent complex formation would enhance gene expression by increasing the amount of free NF-κB to bind to an appropriate DNA sequence, while those that stabilize the complex would prevent or retard gene expression by regulating the amount of free NF-κB available.

For example, to identify chemicals that inhibit complex formation, the IκB DNA sequence in the expression plasmid, pcDNA 1, would be used to generate RNA using SP6 RNA polymerase. The RNA may be translated in a rabbit reticulocyte lysate mixture in the presence of $^{35}$S-methionine, and an aliquot combined with NF-κB in the presence or absence of chemicals being tested for inhibitory activity. A source of NF-κB would be stimulated Jurkat T-cells, prepared as described above. The reaction products could then be analyzed in a gel mobility shift assay. Chemicals that inhibit complex formation would produce little or no shift in the gel assay compared to the control.

To identify chemicals that stabilize the IκB/NF-κB complex, chemicals can be tested for their capacity to maintain the complex in the presence of deoxycholate. The assays for dissociating the IκB/NF-κB complex in deoxycholate/NP40 are described in Example 3, and the instant assay would be conducted similarly but with the addition of the chemical being tested followed by a gel shift assay. Chemicals that stabilize the complex would prevent IκB dissociation from NF-κB and this would be detected by reduced binding of NF-κB to the radiolabelled MHC Class I enchancer probe.

Although any similar or equivalent methods and materials may be employed in the practice or testing of the present invention, the preferred methods and materials are now described. The following examples are illustrative of this invention. They are not intended to be limiting upon the scope thereof.

The present invention has been described with reference to specific embodiments. However, this application is intended to cover those changes and substitutions which may be made by those skilled in the art without departing from the spirit and the scope of the appended claims.

Deposit of Biological Materials: The following plasmid which encodes IκB have been deposited with the American Type Culture Collection.

| Designation | ATCC No. | Date of Deposit |
| --- | --- | --- |
| pC3.A in the E. coli host DH5 | 68622 | 5-16-91 |

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 5 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

ATTA 5

(2) INFORMATION FOR SEQ ID NO:2:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

TGGGGATTCC CCA 13

(2) INFORMATION FOR SEQ ID NO:3:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

Asp Glu Glu Tyr Glu Gln Met Val Lys
1               5

(2) INFORMATION FOR SEQ ID NO:4:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

Arg Pro Ser Thr Arg
1               5

(2) INFORMATION FOR SEQ ID NO:5:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

Pro Glu Ser Thr
1

(2) INFORMATION FOR SEQ ID NO:6:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

TGCGGATTCC CGA 13

( 2 ) INFORMATION FOR SEQ ID NO:7:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:7:

GGCTGGGGAT TCCCCATCT      19

( 2 ) INFORMATION FOR SEQ ID NO:8:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:8:

GCTGCGGATT CCCGATCT      18

( 2 ) INFORMATION FOR SEQ ID NO:9:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:9:

ACCCGGTCAC GTGGCCTACA      20

( 2 ) INFORMATION FOR SEQ ID NO:10:

( i ) SEQUENCE CHARACTERISTICS:
    ( A ) LENGTH: 8 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:10:

ATGCAAAT      8

( 2 ) INFORMATION FOR SEQ ID NO:11:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:11:

CAGAGGGACT TTCCGAGA      18

( 2 ) INFORMATION FOR SEQ ID NO:12:

( i ) SEQUENCE CHARACTERISTICS:
    ( A ) LENGTH: 20 base pairs (B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:12:

TCGTCCGCGC CATGTTCCAG 20

(2) INFORMATION FOR SEQ ID NO:13:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:13:

GACTGGTACC TTCACTAGGC G 21

(2) INFORMATION FOR SEQ ID NO:14:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:14:

TAGAGCAACC TAAACAGAG 19

(2) INFORMATION FOR SEQ ID NO:15:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:15:

CATTCGTGCT TCCAGTGT 18

(2) INFORMATION FOR SEQ ID NO:16:

(i) SEQUENCE CHARACTERISTICS:
(A) LENGTH: 350 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:16:

| | | | | | | |
|---|---|---|---|---|---|---|
| CTGACCTGGT | GTCACTCCTG | TTGAAGTGTG | GGGCTGATGT | CAACAGAGTT | ACCTACCAGG | 60 |
| GCTATTCTCC | CTACCAGCTC | ACCTGGGGCC | GCCCAAGCAC | CCGGATACAG | CAGCAGCTGG | 120 |
| GCCAGCTGAC | ACTAGAAAAC | CTTCAGATGC | TGCCAGAGAG | TGAGGATGAG | GAGAGCTATG | 180 |
| ACACAGAGTC | AGAGTTCACG | GAGTTCACAG | AGGACGAGCT | GCCCTATGAT | GATGACTGTG | 240 |
| TGTTTGGAGG | CCAGCGTCTG | ACGTTATGAG | CAAAGGGGCT | GAAAGAACAT | GGACTTGCAT | 300 |
| ATTTGTACAA | AAAAAAAGT | TTTATTTTTC | TAAAAAAAAA | AAAAAAAA | | 350 |

( 2 ) INFORMATION FOR SEQ ID NO:17:

( i ) SEQUENCE CHARACTERISTICS:
        ( A ) LENGTH: 1550 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 95..1045

( x i ) SEQUENCE DESCRIPTION: SEQ ID NO:17:

```
TGCCGCCGTC  CCGCCCGCCA  GCGCCCCAGC  GAGGAAGCAG  CGCGCAGCCC  GCGGCCCAGC                   60

GCACCCGCAG  CAGCGCCCGC  AGCTCGTCCG  CGCC ATG TTC CAG GCG GCC GAG                          112
                                         Met Phe Gln Ala Ala Glu
                                          1               5

CGC CCC CAG GAG TGG GCC ATG GAG GGC CCC CGC GAC GGG CTG AAG AAG                          160
Arg Pro Gln Glu Trp Ala Met Glu Gly Pro Arg Asp Gly Leu Lys Lys
            10              15                  20

GAG CGG CTA CTG GAC GAC CGC CAC GAC AGC GGC CTG GAC TCC ATG AAA                          208
Glu Arg Leu Leu Asp Asp Arg His Asp Ser Gly Leu Asp Ser Met Lys
        25              30                  35

GAC GAG GAG TAC GAG CAG ATG GTC AAG GAG CTG CAG GAG ATC CGC CTC                          256
Asp Glu Glu Tyr Glu Gln Met Val Lys Glu Leu Gln Glu Ile Arg Leu
        40              45                  50

GAG CCG CAG GAG GTG CCG CGC GGC TCG GAG CCC TGG AAG CAG CAG CTC                          304
Glu Pro Gln Glu Val Pro Arg Gly Ser Glu Pro Trp Lys Gln Gln Leu
55              60                  65                      70

ACC GAG GAC GGG GAC TCG TTC CTG CAC TTG GCC ATC ATC CAT GAA GAA                          352
Thr Glu Asp Gly Asp Ser Phe Leu His Leu Ala Ile Ile His Glu Glu
                75                  80                  85

AAG GCA CTG ACC ATG GAA GTG ATC CGC CAG GTG AAG GGA GAC CTG GCC                          400
Lys Ala Leu Thr Met Glu Val Ile Arg Gln Val Lys Gly Asp Leu Ala
            90                  95                  100

TTC CTC AAC TTC CAG AAC AAC CTG CAG CAG ACT CCA CTC CAC TTG GCT                          448
Phe Leu Asn Phe Gln Asn Asn Leu Gln Gln Thr Pro Leu His Leu Ala
            105                 110                 115

GTG ATC ACC AAC CAG CCA GAA ATT GCT GAG GCA CTT CTG GGA GCT GGC                          496
Val Ile Thr Asn Gln Pro Glu Ile Ala Glu Ala Leu Leu Gly Ala Gly
    120             125                 130

TGT GAT CCT GAG CTC CGA GAC TTT CGA GGA AAT ACC CCC TTA CAC CTT                          544
Cys Asp Pro Glu Leu Arg Asp Phe Arg Gly Asn Thr Pro Leu His Leu
135             140                 145                 150

GCC TGT GAG CAG GGC TGC CTG GCC AGC GTG GGA GTC CTG ACT CAG TCC                          592
Ala Cys Glu Gln Gly Cys Leu Ala Ser Val Gly Val Leu Thr Gln Ser
                155                 160                 165

TGC ACC ACC CCG CAC CTC CAC TCC ATC CTG AAG GCT ACC AAC TAC AAT                          640
Cys Thr Thr Pro His Leu His Ser Ile Leu Lys Ala Thr Asn Tyr Asn
            170             175                 180

GGC CAC ACG TGT CTA CAC TTA GCC TCT ATC CAT GGC TAC CTG GGC ATC                          688
Gly His Thr Cys Leu His Leu Ala Ser Ile His Gly Tyr Leu Gly Ile
            185                 190                 195

GTG GAG CTT TTG GTG TCC TTG GGT GCT GAT GTC AAT GCT CAG GAG CCC                          736
Val Glu Leu Leu Val Ser Leu Gly Ala Asp Val Asn Ala Gln Glu Pro
    200                 205                 210

TGT AAT GGC CGG ACT GCC CTT CAC CTC GCA GTG GAC CTG CAA AAT CCT                          784
Cys Asn Gly Arg Thr Ala Leu His Leu Ala Val Asp Leu Gln Asn Pro
215             220                 225                 230

GAC CTG GTG TCA CTC CTG TTG AAG TGT GGG GCT GAT GTC AAC AGA GTT                          832
```

```
Asp  Leu  Val  Ser  Leu  Leu  Lys  Cys  Gly  Ala  Asp  Val  Asn  Arg  Val
               235                 240                      245
```

| ACC | TAC | CAG | GGC | TAT | TTC | TCC | TAC | CAG | CTC | ACC | TGG | GGC | CGC | CCA | AGC | 880 |
|---|---|---|---|---|---|---|---|---|---|---|---|---|---|---|---|---|
| Thr | Tyr | Gln | Gly | Tyr | Phe | Ser | Tyr | Gln | Leu | Thr | Trp | Gly | Arg | Pro | Ser | |
| | | | 250 | | | | | 255 | | | | | 260 | | | |

| ACC | CGG | ATA | CAG | CAG | CAG | CTG | GGC | CAG | CTG | ACA | CTA | GAA | AAC | CTT | CAG | 928 |
|---|---|---|---|---|---|---|---|---|---|---|---|---|---|---|---|---|
| Thr | Arg | Ile | Gln | Gln | Gln | Leu | Gly | Gln | Leu | Thr | Leu | Glu | Asn | Leu | Gln | |
| | | 265 | | | | | 270 | | | | | 275 | | | | |

| ATG | CTG | CCA | GAG | AGT | GAG | GAT | GAG | GAG | AGC | TAT | GAC | ACA | GAG | TCA | GAG | 976 |
|---|---|---|---|---|---|---|---|---|---|---|---|---|---|---|---|---|
| Met | Leu | Pro | Glu | Ser | Glu | Asp | Glu | Glu | Ser | Tyr | Asp | Thr | Glu | Ser | Glu | |
| | | 280 | | | | 285 | | | | | 290 | | | | | |

| TTC | ACG | GAG | TTC | ACA | GAG | GAC | GAG | CTG | CCC | TAT | GAT | GAC | TGT | GTG | TTT | 1024 |
|---|---|---|---|---|---|---|---|---|---|---|---|---|---|---|---|---|
| Phe | Thr | Glu | Phe | Thr | Glu | Asp | Glu | Leu | Pro | Tyr | Asp | Asp | Cys | Val | Phe | |
| 295 | | | | 300 | | | | | 305 | | | | | 310 | | |

| GGA | GGC | CAG | CGT | CTG | ACG | TTA | TGAGTGCAAA | GGGGCTGAAA | GAACATGGAC | | | | | | | 1075 |
|---|---|---|---|---|---|---|---|---|---|---|---|---|---|---|---|---|
| Gly | Gly | Gln | Arg | Leu | Thr | Leu | | | | | | | | | | |
| | | | | 315 | | | | | | | | | | | | |

| TTGTATATTT | GTACAAAAAA | AAAGTTTTAT | TTTTCTAAAA | AAAGAAAAAA | GAAGAAAAA | 1135 |
|---|---|---|---|---|---|---|
| TTTAAAGGGT | GTACTTATAT | CCACACTGCA | CACTGCCTAG | CCCAAAACGT | CTTATTGTGG | 1195 |
| TAGGATCAGC | CCTCATTTTG | TTGCTTTTGT | GAACTTTTTG | TAGGGGACGA | GAAAGATCAT | 1255 |
| TGAAATTCTG | AGAAAACTTC | TTTTAAACCT | CACCTTTGTG | GGGTTTTGG | AGAAGGTTAT | 1315 |
| CAAAAATTTC | ATGGAAGGAC | CACATTTTAT | ATTTATTGTG | CTTCGAGTGA | CTGACCCCAG | 1375 |
| TGGTATCCTG | TGACATGTAA | CAGCCAGGAG | TGTTAAGCGT | TCAGTGATGT | GGGGTGAAAA | 1435 |
| GTTACTACCT | GTCAAGGTTT | GTGTTACCCT | CCTGTAAATG | GTGTACATAA | TGTATTGTTG | 1495 |
| GTAATTATTT | TGGTACTTTT | ATGATGTATA | TTTATTAAAG | AGATTTTTAC | AAATG | 1550 |

( 2 ) INFORMATION FOR SEQ ID NO:18:

( i ) SEQUENCE CHARACTERISTICS:
        ( A ) LENGTH: 317 amino acids
        ( B ) TYPE: amino acid
        ( D ) TOPOLOGY: linear ( i i ) MOLECULE TYPE: protein ( x i ) SEQUENCE DESCRIPTION: SEQ ID NO:18:

```
Met  Phe  Gln  Ala  Ala  Glu  Arg  Pro  Gln  Glu  Trp  Ala  Met  Glu  Gly  Pro
 1                  5                   10                      15

Arg  Asp  Gly  Leu  Lys  Lys  Glu  Arg  Leu  Leu  Asp  Asp  Arg  His  Asp  Ser
               20                  25                      30

Gly  Leu  Asp  Ser  Met  Lys  Asp  Glu  Glu  Tyr  Glu  Gln  Met  Val  Lys  Glu
               35                  40                      45

Leu  Gln  Glu  Ile  Arg  Leu  Glu  Pro  Gln  Glu  Val  Pro  Arg  Gly  Ser  Glu
      50                  55                      60

Pro  Trp  Lys  Gln  Gln  Leu  Thr  Glu  Asp  Gly  Asp  Ser  Phe  Leu  His  Leu
 65                      70                      75                      80

Ala  Ile  Ile  His  Glu  Glu  Lys  Ala  Leu  Thr  Met  Glu  Val  Ile  Arg  Gln
                    85                       90                      95

Val  Lys  Gly  Asp  Leu  Ala  Phe  Leu  Asn  Phe  Gln  Asn  Asn  Leu  Gln  Gln
               100                 105                     110

Thr  Pro  Leu  His  Leu  Ala  Val  Ile  Thr  Asn  Gln  Pro  Glu  Ile  Ala  Glu
               115                 120                     125

Ala  Leu  Leu  Gly  Ala  Gly  Cys  Asp  Pro  Glu  Leu  Arg  Asp  Phe  Arg  Gly
               130                 135                     140

Asn  Thr  Pro  Leu  His  Leu  Ala  Cys  Glu  Gln  Gly  Cys  Leu  Ala  Ser  Val
145                      150                     155                     160
```

| | | | | | | | | | | | | | | | |
|---|---|---|---|---|---|---|---|---|---|---|---|---|---|---|---|
| Gly | Val | Leu | Thr | Gln<br>165 | Ser | Cys | Thr | Thr | Pro<br>170 | His | Leu | His | Ser | Ile<br>175 | Leu |
| Lys | Ala | Thr | Asn<br>180 | Tyr | Asn | Gly | His | Thr<br>185 | Cys | Leu | His | Leu | Ala<br>190 | Ser | Ile |
| His | Gly | Tyr<br>195 | Leu | Gly | Ile | Val | Glu<br>200 | Leu | Leu | Val | Ser | Leu<br>205 | Gly | Ala | Asp |
| Val | Asn<br>210 | Ala | Gln | Glu | Pro | Cys<br>215 | Asn | Gly | Arg | Thr | Ala<br>220 | Leu | His | Leu | Ala |
| Val<br>225 | Asp | Leu | Gln | Asn | Pro<br>230 | Asp | Leu | Val | Ser | Leu<br>235 | Leu | Leu | Lys | Cys | Gly<br>240 |
| Ala | Asp | Val | Asn | Arg<br>245 | Val | Thr | Tyr | Gln | Gly<br>250 | Tyr | Phe | Ser | Tyr | Gln<br>255 | Leu |
| Thr | Trp | Gly | Arg<br>260 | Pro | Ser | Thr | Arg | Ile<br>265 | Gln | Gln | Gln | Leu | Gly<br>270 | Gln | Leu |
| Thr | Leu | Glu<br>275 | Asn | Leu | Gln | Met | Leu<br>280 | Pro | Glu | Ser | Glu | Asp<br>285 | Glu | Glu | Ser |
| Tyr | Asp<br>290 | Thr | Glu | Ser | Glu | Phe<br>295 | Thr | Glu | Phe | Thr | Glu<br>300 | Asp | Glu | Leu | Pro |
| Tyr<br>305 | Asp | Asp | Cys | Val | Phe<br>310 | Gly | Gly | Gln | Arg | Leu<br>315 | Thr | Leu | | | |

We claim:

1. A method of identifying a chemical that increases dissociation of an NF-κB/IκB complex, comprising the steps of:
   a) expressing a nucleic acid encoding an IκB protein having the sequence set forth as SEQ ID NO: 18;
   b) purifying said IκB protein;
   c) preparing a complex comprising said IκB protein and an NF-κB protein and contacting the complex with said chemical; and
   d) identifying said chemical as a chemical that increases dissociation of said NF-κB/IκB complex by its capacity to dissociate the complex of step c).

2. A method of identifying a chemical that decreases dissociation of an NP-κB/κB complex, comprising the steps of:
   a) expressing a nucleic acid encoding an IκB protein having the sequence set forth as SEQ ID NO: 18;
   b) purifying said IκB protein;
   c) combining in solution an NF-κB protein, said IκB protein, and said chemical, said IκB protein and said NF-κB protein being present in amounts sufficient to form a complex comprising said IκB protein and i NF-κB protein; and
   d) identifying said chemical as a chemical that decreases dissociation of said NF-κB/IκB complex by its capacity to prevent or retard the dissociation of aid IκB protein from the complex of step c).

3. The method according to claim 2 further comprising adding a dissociating agent to the solution of step c).

4. The method according to claim 3 wherein said dissociating agent is a detergent.

5. The method according to claim 4 wherein said detergent is sodium deoxycholate.

6. The method according to claim 4 wherein said detergent is NP40.

* * * * *